United States Patent
Lee et al.

(10) Patent No.: US 12,083,140 B2
(45) Date of Patent: *Sep. 10, 2024

(54) PHARMACEUTICAL COMPOSITION FOR PREVENTING AND TREATING GLAUCOMA, CONTAINING ADENOSINE DERIVATIVE

(71) Applicant: FUTURE MEDICINE CO., LTD., Seongnam-si (KR)

(72) Inventors: Sang Koo Lee, Seoul (KR); Chong Woo Park, Seoul (KR); Hea Ok Kim, Seoul (KR); Hee Woo Lee, Seoul (KR); Mi Ra Yu, Seoul (KR)

(73) Assignee: FUTURE MEDICINE CO., LTD., Seongnam-si (KR)

( * ) Notice: Subject to any disclaimer, the term of this patent is extended or adjusted under 35 U.S.C. 154(b) by 28 days.

This patent is subject to a terminal disclaimer.

(21) Appl. No.: 17/458,231

(22) Filed: Aug. 26, 2021

(65) Prior Publication Data

US 2021/0386771 A1  Dec. 16, 2021

Related U.S. Application Data

(63) Continuation of application No. 16/492,938, filed as application No. PCT/KR2018/003274 on Mar. 21, 2018, now Pat. No. 11,185,556.

(30) Foreign Application Priority Data

Mar. 21, 2017 (KR) .................. 10-2017-0035224

(51) Int. Cl.
| | | |
|---|---|---|
| *A61K 31/7076* | (2006.01) | |
| *A61K 9/00* | (2006.01) | |
| *A61P 27/06* | (2006.01) | |

(52) U.S. Cl.
CPC ........ *A61K 31/7076* (2013.01); *A61K 9/0019* (2013.01); *A61K 9/0053* (2013.01); *A61P 27/06* (2018.01)

(58) Field of Classification Search
CPC .............. A61K 31/7076; A61K 9/0019; A61K 9/0053; A61P 27/06
USPC .......................................... 514/46
See application file for complete search history.

(56) References Cited

U.S. PATENT DOCUMENTS

| 9,018,371 | B2 | 4/2015 | Jeong | |
|---|---|---|---|---|
| 11,185,556 | B2 * | 11/2021 | Lee | ........ A61K 31/52 |
| 11,266,644 | B2 * | 3/2022 | Kim | ........ A61K 31/5025 |
| 2009/0258836 | A1 | 10/2009 | Civan | |
| 2010/0137577 | A1 | 6/2010 | Jeong et al. | |

FOREIGN PATENT DOCUMENTS

| JP | 2010-505848 A | 2/2010 |
|---|---|---|
| JP | 2010-520271 A | 6/2010 |
| KR | 10-1805400 B1 | 12/2017 |
| WO | 2008-045330 A2 | 4/2008 |
| WO | 2012-125400 A1 | 9/2012 |

OTHER PUBLICATIONS

International Search Report for PCT/KR2018/003274 mailed Jun. 28, 2018 from Korean Intellectual Property Office.
Jacobson, K. A. et al., "Adenosine Receptors: Pharmacology, Structure-Activity Relationships, and Therapeutic Potential", J. Med. Chem., 35, 407-422, 1992.
Zhou, Q. Y, et al., "Molecular cloning and characterization of an adenosine receptor: The A3 adenosine receptor", Proc. Natl. Acad. Sci., U.S.A., 89, 7432-7436, 1992.
Ramkumar, V. et al., "The A3 Adenosine Receptor Is the Unique Adenosine Receptor Which Facilitates Release of Allergic Mediators in Mast Cells", J. Biol. Chem., 268, 168871-168890, 1993.
Abbracchio, M. P. et al., "G protein-dependent activation of phospholipase C by adenosine A3 receptors in rat brain", Mol. Pharmacol., 48, 1038-1045, 1995.
Baraldi, P. G. et al., "Pyrazolo[4,3-e]1,2,4-Triazolo[1,5-c]Pyrimidine Ligands, New Tools to Characterize A3 Adenosine Receptors in Human Tumor Cell Lines", Curr. Med. Chem., 12, 1319-1329, 2005.
Kim, S-K. et al., "Docking studies of agonists and antagonists suggest an activation pathway of the A3 adenosine receptor", J. Mol. Graph. Model., 25, 562-577, 2006.
Wang, Z. et al., "Nucleoside-derived antagonists to A3 adenosine receptors lower mouse intraocular pressure and act across species", Experimental Eye Research, 2010 [Electronic publishing Oct. 28, 2009], vol. 90, No. 1, pp. 146-154.
Zhao Wang et al., "Nucleoside-derived antagonists to A3 adenosine receptors lower mouse intraocular pressure and act across species", Experimental Eye Research, Jan. 2010, vol. 90, No. 1, pp. 146-154.
Yisheng Zhong et al. "Adenosine, adenosine receptors and glaucoma: An updated overview", Biochimica et Biophysica Acta (BBA), vol. 1830, Issue 4, Apr. 2013, pp. 2882-2890.
Glossary of medical education terms, Institute of International Medical Education. http://www.iime.org/glossary.htm Accessed in Mar. 2013. (Year: 2013).
Zhong et al. Adenosine, adenosine receptors and glaucoma: An updated overview. Biochimica et Biophysica Acta 1830 (2013) 2882-2890. (Year: 2013).
Van Troostenburg et al. Tolerability, pharmacokinetics and concentration-dependent hemodynamic effects of oral CF101, an A3 adenosine receptor agonist, in healthy young men. International Journal of Clinical Pharmacology and Therapeutics, vol. 42, No. 10 , p. 534-542, 2004. (Year: 2004).
Lee et al. The Relationship Between Diabetic Retinopathy and Diabetic Nephropathy in a Population-Based Study in Korea ( KN HAN ES V-2, 3). Invest Ophthalmol Vis Sci 55:6547-6553, 2014. (Year: 2014).

(Continued)

*Primary Examiner* — Yih-Horng Shiao
(74) *Attorney, Agent, or Firm* — Revolution IP, PLLC

(57) ABSTRACT

A pharmaceutical composition for preventing or treating eye diseases and an oral administration agent for preventing or treating eye diseases are provided, wherein the pharmaceutical composition for preventing or treating eye diseases includes the compound represented by Chemical Formula 1 or a pharmaceutically acceptable salt thereof as an active ingredient.

5 Claims, 18 Drawing Sheets

(56) References Cited

OTHER PUBLICATIONS

Hyuk Woo Lee et al., "Design, synthesis, and binding of homologated truncated 4'-thioadenosine derivatives at the human A3 adenosine receptors", Bioorganic & Medicinal Chemistry, vol. 18, Issue 19, Oct. 1, 2010, pp. 7015-7021.
Lak Shin Jeong et al, "Discovery of a new nucleoside template for human A3 adenosine receptor ligands: D-4'-thioadenosine derivatives without 4'-hydroxymethyl group as highly potent and selective antagonists1", Journal of Medical Chemistry, vol. 50, No. 14, Jul. 12, 2007, pp. 3159-3162.
Lak Shin Jeong et al, "Structure-Activity Relationships of Truncated D- and L-4'-Thioadenosine Derivatives as Species-Independent A3 Adenosine Receptor Antagonists", Journal of Medical Chemistry, vol. 51, No. 20, Sep. 24, 2008, pp. 6609-6613.

\* cited by examiner

PHARMACEUTICAL COMPOSITION FOR PREVENTING AND TREATING GLAUCOMA, CONTAINING ADENOSINE DERIVATIVE

CROSS REFERENCE TO PRIOR APPLICATIONS

This application is a Continuation Application of U.S. patent application Ser. No. 16/492,938 filed on Sep. 10, 2019 under 35 U.S.C. § 120, which is the 35 U.S.C. 371 national stage of International application PCT/KR2018/003274 filed on Mar. 21, 2018; which claims priority to Korean Patent Application No. 10-2017-0035224 filed on Mar. 21, 2017. The entire contents of each of the above-identified applications are hereby incorporated by reference.

BACKGROUND

The present invention relates to a pharmaceutical composition comprising an adenosine derivative which can be effectively used for preventing or treating eye diseases and further for preventing or treating the elevation of the intraocular pressure and glaucoma.

Adenosine is a substance which performs many physiological functions through specific cell membrane receptors and extracellular adenosine acts as a neurotransmitter in many physiological systems, and in general, it compensates for the hyperactivity of a given organ and protects from the harmful effects of stress (Jacobson, K. A. et al., J. Med. Chem., 35, 407-422, 1992). This effect is due to a partially generated negative feedback loop that reduces the energy requirement of the cell by adenosine produced by the degradation of intracellular or extracellular ATP (adenosine triphosphate) and increases the supply of oxygen. Adenosine is important for maintaining the homeostasis of essential organs such as the brain, heart, and kidney and for example, administration of adenosine agonist from the outside to the brain has been shown to have a neuroprotective action, and it is known that it is also involved in pain, cognition, exercise or sleep.

Adenosine receptors are now classified as P1 and P2 receptors, respectively, by pharmacological studies and molecular cloning. The P1 receptor acts as a substrate for adenosine and the P2 receptor acts as a substrate for ATP, ADP, UTP and UDP to express physiological activity. Among these, as for the P1 receptors, four different subtypes of adenosine receptors have been identified and classified into $A_1$, $A_2$ or $A_3$ according to affinity to ligand, body distribution and action pathway, etc. and $A_2$ is again classified into $A_{2A}$ and $A_{2B}$. These adenosine receptors are a class of G-protein-coupled receptor family, and the adenosine $A_1$, $A_{2A}$ and $A_{2B}$ receptors have been pharmacologically confirmed using many selective ligands, but the adenosine $A_3$ receptor was first identified in 1992 (Zhou, Q. Y, et al., Proc. Natl. Acad. Sci., USA, 89, 7432-7436, 1992), and many studies have been performed to confirm the pathophysiological function of this receptor.

Adenosine $A_1$ and $A_2$ receptor agonists are mainly derivatives of adenosine and have been extensively studied as antihypertensive agents, antipsychotic agents, antiarrhythmic agents, lipid metabolism inhibitors (diabetic agents), and brain protectants, and antagonists thereof are xanthine derivatives, or in which a plurality of bicyclic molecule is joined together and are developed as an asthma treatment agent, an antidepressant, an arrhythmia agent, a nephrotoxic agent, a Parkinson's disease treatment agent or an smart drug and the like. Nevertheless, currently commercialized is only adenosine itself which is in use for treating supraventricular tachycardia; and dipyridamole, an adenosine transport inhibitor which is in use as a warfarin adjuvant for preventing blood coagulation following cardiac surgery. The reasons why commercialization is not smooth that the adenosine receptor is spread throughout the body and is due to the various pharmacological actions involved in activating the receptor, i.e., there is no compound that can activate only the adenosine receptor of the desired tissue.

Among the adenosine receptors, the adenosine $A_3$ receptor is the most recently recognized receptor, unlike the well-known adenosine $A_1$ and $A_2$ receptors, and its role is not well known and many studies are in progress to develop a selective receptor modulator. To investigate the adenosine $A_3$ receptor pharmacologically, three radiolabeled ligands such as [$^{125}$I]ABA($N^6$-(4-amino-3-[$^{125}$I]iodobenzyl)-adenosine, $N^6$-(4-amino-3-[$^{125}$I]iodobenzyl)-adenosine), [$^{125}$I] APNEA($N^6$-2-(4-amino-3-[$^{125}$I]iodophenyl)-ethyladenosine, $N^6$-2-(4-amino-3-[$^{125}$I]iodophenyl)-ethyladenosine) or [$^{125}$I]AB-MECA(($N^6$-(4-amino-3-[$^{125}$I]iodobenzyl)-adenosine-5'-N-methylcarboxamide, $N^6$-(4-amino-3-[$^{125}$I]iodobenzyl)-adenosine-5'-N-methylcarboxamide), have been used. It proved that when the adenosine $A_3$ receptor is expressed in Chinese hamster ovary (CHO) cells through pharmacological studies using the radiolabeled ligand, the $A_3$ receptor has function of inhibiting adenylyl cyclase, an enzyme that produces cAMP from ATP adenylyl cyclase, and when the $A_3$ receptor is activated by an agonist, it cleaves phosphatidyl inositol in the brain to activate GTP-dependent phospholipase C (Guanosine triphosphate-dependent phospholipase C), an enzyme producing inositol phosphate and DAG (Ramkumar, V. et al., J. Biol. Chem., 268, 168871-168890, 1993; Abbracchio, M P et al., Mol. Pharmacol., 48, 1038-1045, 1995). This finding can explain the possibility of a pathway of $A_3$ receptor activation by brain ischemia, since this secondary messenger system represents the response pathway of neuronal injury in cerebral ischemia. In addition, it is known that the $A_3$ receptor agonists inhibit the release of the tumor necrosis factor TNF-α (tumor necrosis factor-α), which is an inflammatory mediator, and also inhibit the production of the inflammatory mediators such as MIP-1α, interleukin-12 and interferon-γ, and it has a protective effect against the heart as well as a protective effect against brain diseases such as epilepsy. On the other hand, inactivation of the adenosine $A_3$ receptor causes the release of inflammatory factors such as histamine from mast cells, contracts the bronchi and causes apoptosis in immune cells. Accordingly, adenosine $A_3$ antagonists have potential for development as anti-inflammatory agents and asthma treatment agents. Therefore, if a compound having pharmacological selectivity can be developed, it would be possible to develop new therapeutic drugs for various diseases such as asthma, inflammation, cerebral ischemia, heart disease, cancer, etc.

Among the substances that have been researched and developed so far, representative human adenosine $A_3$ agonists include $N^6$-(3-iodobenzyl)-5'-(N-methylcarbamoyl)-adenosine (B-MECA) and $N^6$-(3-iodobenzyl)-2-chloro-5'-(N-methylcarbamoyl)-adenosine (CI-IB-MECA) and has a high affinity and selectivity for the $A_3$ receptor as compared to the adenosine $A_1$ and $A_2$ receptors. On the other hand, it has been pointed out that because the adenosine $A_3$ antagonist exhibiting high affinity and selectivity is mostly a nonpurine bicyclic compound, not a nucleoside skeleton and exhibits high activity in human receptors, but weak or little activity in rat $A_3$ receptor, it is impossible to carry out animal experiments essential for the development of drugs which can be clinically applied (Baraldi, P G et al., Curr. Med. Chem., 12, 1319-1329, 2005). However, because nucleoside-based compounds exhibit high affinity and selectivity regardless of species, as compared with non-purine bicyclic compounds to have an advantage of easy experiment with animals, the possibility of development as a new drug is considered to be very high and therefore, it is an urgent task to elucidate the selective $A_3$ antagonist of this series.

In order to act as an agonist of the adenosine $A_3$ receptor through analysis of various previous studies, the present inventors have found that the N-methyl carbamoyl group at 5-position of the sugar in the structure of IB-MECA and CI-IB-MECA should be essentially present and that the base moiety should be substituted with an arylamino group or an alkylamino group at 6-position of purine. Therefore, the N-methylcarbamoyl group at the 5-position of the sugar causes a conformational change essential for the agonist action of the receptor through hydrogen bonding (Kim, S-K. et al., J. Mol., 25, 562-577, 2006), it is considered that synthesis of a substance in which N-methylcarbamoyl group at the 5-position of the sugar is removed can be developed as an $A_3$ receptor antagonist.

Meanwhile, glaucoma, a type of eye disease, is a disease that can be induced by intraocular pressure elevation due to the problem of the production or release mechanism of aqueous humor. It is globally recognized as a serious disease because the intraocular pressure elevation can cause an abnormality in the function of the optic nerve due to disorder of blood supply and can lead to blindness at the end.

Therefore, the present inventors have firstly studied an adenosine $A_3$ receptor antagonist as an agent for preventing and treating glaucoma which is caused by an elevation of the intraocular pressure and which may be accompanied by such symptoms, and synthesized novel adenosine derivative compounds capable of effectively lowering intraocular pressure by inhibiting the production of aqueous humor in the ciliary body and remodeling the trabecular meshwork tissue by promoting anti-fibrosis,

SUMMARY

A problem to be solved by the present invention is to provide a pharmaceutical composition comprising an adenosine derivative which acts as an adenosine $A_3$ receptor antagonist capable of preventing or treating eye diseases such as intraocular pressure elevation and glaucoma and the like.

The problems of the present invention are not limited to the above-mentioned technical problems and other technical problems which are not mentioned may be clearly understood by those skilled in the art from the description below.

In order to solve the above problems, a pharmaceutical composition for preventing or treating eye diseases according to an embodiment of the present invention comprises a compound represented by following Chemical Formula 1 or a pharmaceutically acceptable salt thereof as an active ingredient:

[Chemical Formula 1]

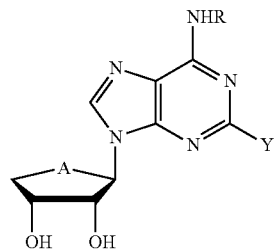

wherein A is S,

R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen and one or more linear or branched $C_1$-$C_4$ alkoxy groups, or a hydroxycarbonyl-substituted benzyl, and Y is H or a halogen element.

Also, the eye diseases may include at least one of intraocular pressure elevation and glaucoma.

In addition, the compound represented by the Chemical Formula 1 may be a compound represented by the Chemical Formula A:

[Chemical Formula A]

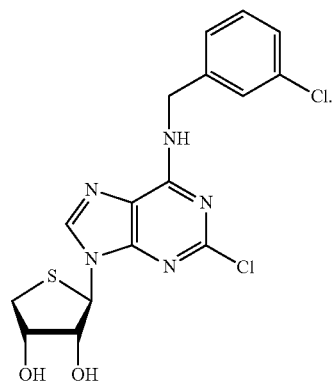

In order to solve the above other problems, an oral administration agent for preventing or treating eye diseases according to an embodiment of the present invention comprises a compound represented by following Chemical Formula 1 or a pharmaceutically acceptable salt:

[Chemical Formula 1]

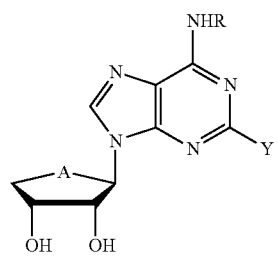

wherein A is S,

R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen and one or more linear or branched $C_1$-$C_4$ alkoxy groups, or a hydroxycarbonyl-substituted benzyl, and Y is H or a halogen element.

Also, the eye diseases may include at least one of intraocular pressure elevation and glaucoma.

In addition, the oral administration agent may further comprise an excipient comprising at least one selected from the group consisting of methyl cellulose (MC), dimethyl sulfoxide (DMSO), polyethylene glycol (PEG) and distilled water.

Furthermore, the excipient may comprise 0.5 wt % of methyl cellulose.

In addition, the compound represented by the Chemical Formula 1 or a pharmaceutically acceptable salt thereof may be filled in capsules in powder form.

In addition, the compound represented by the Chemical Formula 1 may be a compound represented by the Chemical Formula A:

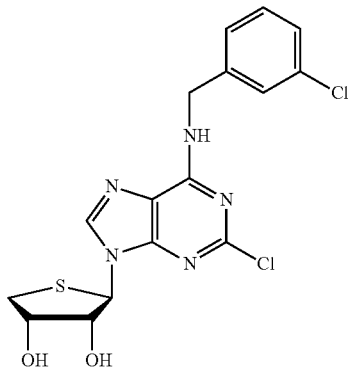

[Chemical Formula A]

The details of other embodiments are included in the detailed description and drawings.

An adenosine derivative of the present invention can act as an adenosine $A_3$ receptor antagonist capable of preventing or treating eye diseases such as the elevation of the intraocular pressure and glaucoma, and is thus suitable for prevention and treatment of eye diseases, and it can be used as a pharmaceutical composition which is very suitable for oral administration for preventing and treating eye diseases because it is excellent in absorption of the drug when administered orally, biocompatible with little toxicity in the body, and superior in storage stability when formulated as an oral administration agent.

Also, the adenosine derivatives of the present invention can be used as a pharmaceutical composition highly suitable for preventing and treating glaucoma, because they have a dual pharmacological mechanism of inhibiting the production of an aqueous humor in the ciliary body and promoting the release of the aqueous humor through remodeling of trabecular meshwork tissue by the promotion of anti-fibrosis.

The effects according to the embodiments of the present invention are not limited by the contents exemplified above, and more various effects are included in the present specification.

DETAILED DESCRIPTION

Figure 1:
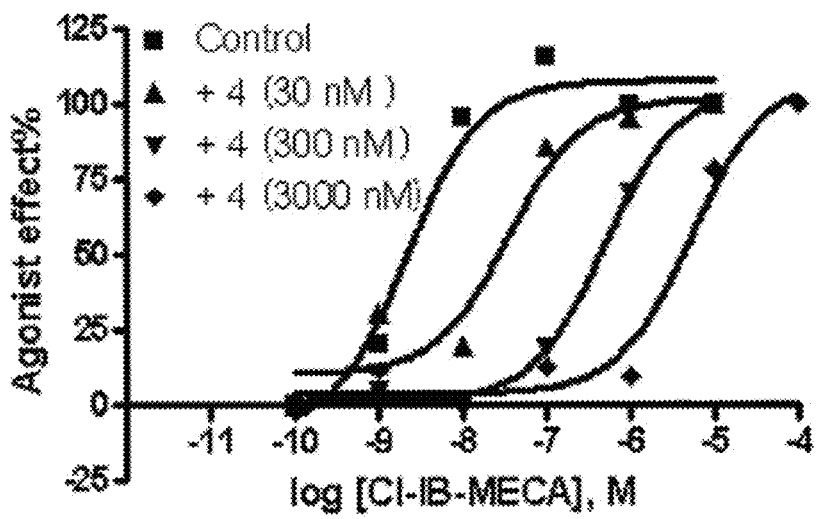
FIG. 1 shows the antagonistic effect of the compound of Example 4 of the present invention on Chinese hamster ovary (CHO) cells treated with CI-IB-MECA as an agonist.

Hereinafter, the present invention will be described in detail.

The present invention provides an adenosine derivative comprising a compound represented by the following Chemical Formula 1 or a pharmaceutically acceptable salt thereof, as an active ingredient:

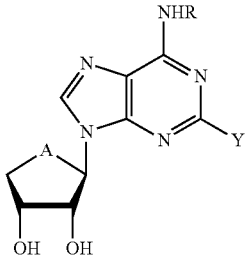

[Chemical Formula 1]

wherein A is O or S,
R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen and one or more linear or branched $C_1$-$C_4$ alkoxy groups, or a hydroxycarbonyl-substituted benzyl, and
Y is H or a halogen element.

Preferably, the A is O or S, the R is methyl, ethyl, propyl, naphthylmethyl, benzyl, benzyl substituted independently or optionally by one or at least two substituents selected from the group consisting of F, Cl, Br, I and $C_1$-$C_3$ alkoxy or toluic acid, and the Y is H or Cl.

More preferably, the A is O or S, the R is selected from the group consisting of methyl, ethyl, 1-naphthylmethyl, benzyl, 2-chlorobenzyl, 3-fluorobenzyl, 3-chlorobenzyl, 3-bromobenzyl, 3-iodobenzyl, 2-methoxy-5-chlorobenzyl, 2-methoxybenzyl or 3-toluol acid, and the Y is H or Cl.

Preferred examples of the adenosine derivatives represented by the above Chemical Formula 1 according to the present invention are as follows:
1) (2R,3R,4S)-2-(2-chloro-6-(3-fluorobenzylamino)-9H-purin-9-yl) tetrahydrothiophene-3,4-diol;
2) (2R,3R,4S)-2-(2-chloro-6-(3-chlorobenzylamino)-9H-purin-9-yl) tetrahydrothiophene-3,4-diol;
3) (2R,3R,4S)-2-(6-(3-bromobenzylamino)-2-chloro-9H-purin-9-yl)tetrahydrothiophene-3,4-diol;
4) (2R,3R,4S)-2-(2-chloro-6-(3-iodobenzylamino)-9H-purin-9-yl)tetrahydrothiophene-3,4-diol;
5) (2R,3R,4S)-2-(2-chloro-6-(2-chlorobenzylamino)-9H-purin-9-yl)tetrahydrothiophene-3,4-diol;
6) (2R,3R,4S)-2-(2-chloro-6-(5-chloro-2-methoxybenzylamino)-9H-purin-9-yl)tetrahydrothiophene-3,4-diol;
7) (2R,3R,4S)-2-(2-chloro-6-(2-methoxybenzylamino)-9H-purin-9-yl)tetrahydrothiophene-3,4-diol;
8) (2R,3R,4S)-2-(2-chloro-6-(naphthalen-1-ylmethylamino)-9H-purin-9-yl)tetrahydrothiophene-3,4-diol;
9) 3-((2-chloro-9-((2R,3R,4S)-3,4-dihydroxytetrahydrothiophen-2-yl)-9H-purin-6-ylamino)methyl)benzoic acid;
10) 2-(2-chloro-6-methylamino-purin-9-yl)tetrahydrothiophene-3,4-diol;
11) (2R,3R,4S)-2-(6-(3-fluorobenzylamino)-9H-purin-9-yl) tetrahydrothiophene-3,4-diol;
12) (2R,3R,4S)-2-(6-(3-chlorobenzylamino)-9H-purin-9-yl)tetrahydrothiophene-3,4-diol;
13) (2R,3R,4S)-2-(6-(3-bromobenzylamino)-9H-purin-9-yl)tetrahydrothiophene-3,4-diol;
14) (2R,3R,4S)-2-(6-(3-iodobenzylamino)-9H-purin-9-yl)tetrahydrothiophene-3,4-diol;
15) (2R,3R,4R)-2-(6-(3-bromobenzylamino)-2-chloro-9H-purin-9-yl)tetrahydrofiran-3,4-diol; and
16) (2R,3R,4R)-2-(2-chloro-6-(3-iodobenzylamino)-9H-purin-9-yl)tetrahydrofuran-3,4-diol.

The adenosine derivative represented by the Chemical Formula 1 according to the present invention may be used in the form of a pharmaceutically acceptable salt. As the salt, an acid addition salt formed by various pharmaceutically acceptable organic acids or inorganic acids is useful. Suitable organic acids include, for example, organic acids such as carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methylsulfuric acid, ethylsulfuric acid and dodecylsulfuric acid, etc. and suitable inorganic acids include, for example, hydrogen acids such as hydrochloric acid, sulfuric acid or phosphoric acid.

The adenosine derivatives represented by Chemical Formula 1 according to the present invention may include not only pharmaceutically acceptable salts, but also all salts, hydrates and solvates which can be prepared by conventional methods.

Also, the present invention provides a method of preparing the adenosine derivative represented by the above Chemical Formula 1.

Specifically, as shown in Reaction Scheme 1 below, the present invention provides a method of preparing the adenosine derivative represented by the above Chemical Formula 1 comprising: obtaining β-anomer compound of Chemical Formula 3 by reacting a compound of Chemical Formula 2 as a starting material with a silylated purine compound in the presence of a Lewis acid catalyst (Step 1); obtaining a diol compound of Chemical Formula 4 by adding hydrochloric acid to the compound of the Chemical Formula 3 obtained in the step 1 (Step 2); and obtaining an adenosine derivative by reacting the diol compound of the Chemical Formula 4 obtained in the step 2 with an amine compound under a base catalyst (Step 3).

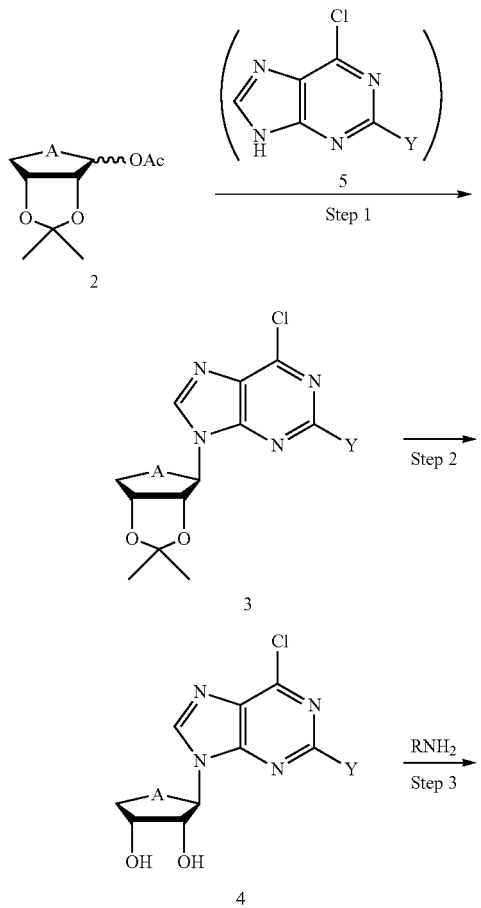

-continued

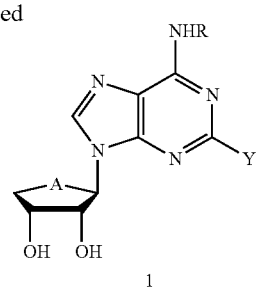

1

In the above Reaction Scheme 1, A, R and Y are as defined in Chemical Formula 1.

Hereinafter, the preparation method of the present invention will be described step by step.

Step 1 according to the present invention is a step of obtaining β-anomer compound of Chemical Formula 3 by reacting a compound of Chemical Formula 2 as a starting material with a silylated purine compound in the presence of a Lewis acid catalyst.

The compound of Chemical Formula 3 may be obtained by reacting the compound of Chemical Formula 2 with a silylated purine compound in the presence of a Lewis acid. As the Lewis acid, trimethylsilyl trifluoromethanesulfonate (TMSOTf) may be used. In addition, as the solvent of the step 1, dichloroethane, chloroform, acetonitrile, dichloromethane and the like are preferably used. Among them, dichloroethane is more preferable. The silylated purine compound can be obtained by reacting the purine compound of Chemical Formula 5 with hexamethyldisilazane (HMDS) and ammonium sulfate catalyst.

Step 2 according to the present invention is a step of obtaining a diol compound of Chemical Formula 4 by adding hydrochloric acid to the compound of the Chemical Formula 3 obtained in the step 1. At this time, acetic acid, sulfuric acid, and p-toluenesulfonic acid may be used instead of hydrochloric acid.

Step 3 according to the present invention is a step of obtaining an adenosine derivative by reacting the diol compound of the Chemical Formula 4 obtained in the step 2 with an amine compound under a base catalyst.

As the base catalyst, triethylamine, pyridine, N, N-dimethylaminopyridine, 1,4-dioxane and the like are preferably used, and among them, triethylamine is more preferable. Further, as the solvent in the step 3, a solvent such as lower alcohol including methanol and ethanol or 1,4-dioxane, tetrahydrofuran and chloroform is preferable.

In the method for preparing an adenosine derivative of the present invention, the compound of Chemical Formula 2 as a starting material may be prepared according to the following Reaction Scheme 2 or 3 according to the type of substituent A.

When A is sulfur (S), as shown in Reaction Scheme 2 below, it comprises: obtaining a diacetonide compound of Chemical Formula 7 by reacting D-mannose compound of Chemical Formula 6 with 2,2-dimethoxypropane under acid catalysis (Step $a_1$); obtaining a diol compound of Chemical Formula 8 by ring cleavage of the compound of Chemical Formula 7 obtained in the step $a_1$ in the presence of a reducing agent (Step $a_2$); obtaining a dimesyl compound of Chemical Formula 9 by mesylating the compound of Chemical Formula 8 obtained in the step $a_2$ (Step $a_3$); obtaining a thiosugar compound of Chemical Formula 10 by cyclizing the compound of Chemical Formula 9 obtained in the step $a_3$ (Step $a_4$); obtaining a diol compound of Chemical Formula 11 by selectively hydrolyzing the compound of Chemical Formula 10 obtained in the step $a_4$ (Step $a_5$); and obtaining an acetate compound of Chemical Formula 2a by reacting the compound of Chemical Formula 11 obtained in the step as in the presence of a catalyst (Step $a_6$).

[Reaction Scheme 2]

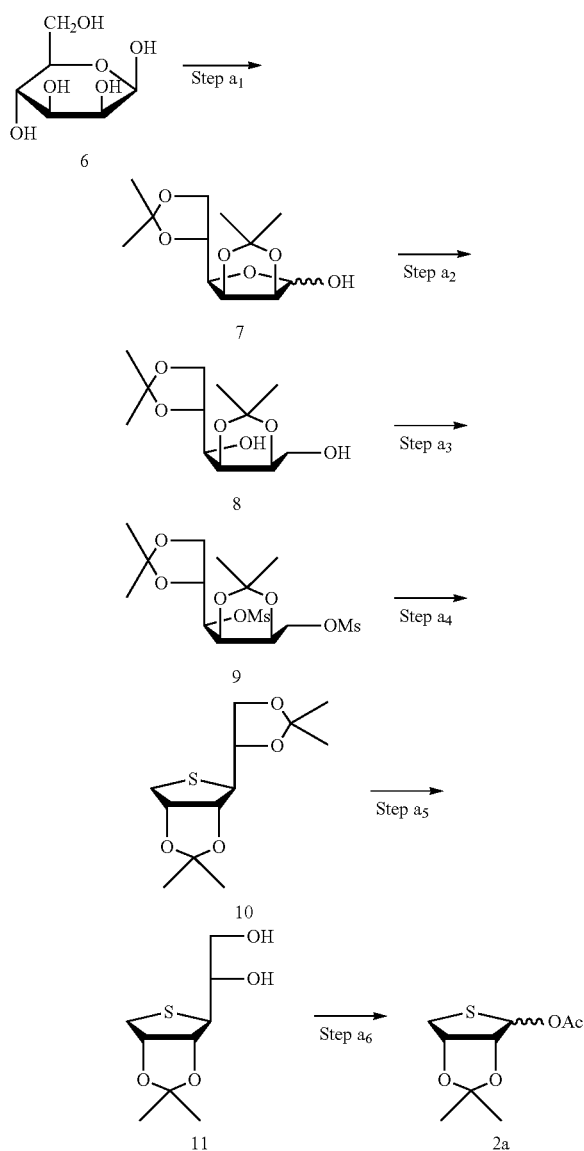

(In the above Reaction Scheme 2, compound 2a is a compound of Chemical Formula 2.)

Hereinafter, the preparation method for the compound of Chemical Formula 2 of the present invention will be described in detail step by step.

Step $a_1$ according to the method of preparing a compound of Chemical Formula 2 of the present invention is a step of obtaining a diacetonide compound of Chemical Formula 7 by reacting D-mannose compound of Chemical Formula 6 with 2,2-dimethoxypropane under acid catalysis.

The compound of Chemical Formula 7 can be obtained by reacting D-mannose of Chemical Formula 6 with 2,2-dimethoxypropane in the presence of an acid catalyst and acetic anhydride and as the acid catalyst, inorganic acids such as concentrated sulfuric acid or hydrochloric acid gas or organic acids such as p-toluenesulfonic acid can be used.

Step $a_2$ according to the method of preparing a compound of Chemical Formula 2 of the present invention is a step of obtaining a diol compound of Chemical Formula 8 by ring cleavage of the compound of Chemical Formula 7 obtained in the step $a_1$ in the presence of a reducing agent The compound of Chemical Formula 8 can be obtained by reacting with a reducing agent, sodium borohydride. Instead of the sodium borohydride, a metal hydride such as lithium aluminum hydride, sodium sulfite or the like may be used.

Step $a_3$ according to the method of preparing a compound of Chemical Formula 2 of the present invention is a step of obtaining a dimesyl compound of Chemical Formula 9 by mesylating the compound of Chemical Formula 8 obtained in the step $a_2$.

The compound of Chemical Formula 9 can be obtained by reacting the compound of Chemical Formula 8 with methanesulfonyl chloride (MsCl), and as the reaction solvent, ethyl ether, petroleum ether, dichloromethane, tetrahydrofuran and inert solvent such as N, N-dimethylformamide can be preferably used.

Step $a_4$ according to the method of preparing a compound of Chemical Formula 2 of the present invention is a step of obtaining a thiosugar compound of Chemical Formula 10 by cyclizing the compound of Chemical Formula 9 obtained in the step $a_3$.

The compound of Chemical Formula 10 can be obtained by reacting the compound of Chemical Formula 9 with sodium sulfide and substitution reaction with thioester such as methyl thioacetate in place of sodium sulfide, is followed by reaction with sodium alkoxide or the like. As the solvent in the step $a_4$, N,N-dimethylformamide, dimethylsulfoxide and the like can be used.

Step as according to the method of preparing a compound of Chemical Formula 2 of the present invention is a step of obtaining a diol compound of Chemical Formula 11 by selectively hydrolyzing the compound of Chemical Formula 10 obtained in the step $a_4$.

The compound of Chemical Formula 11 can be obtained by selectively hydrolyzing 5,6-acetonide by using acetic acid and sulfuric acid, hydrochloric acid, p-toluenesulfonic acid and the like may be used instead of acetic acid.

The step $a_6$ according to the method of preparing a compound of Chemical Formula 2 of the present invention is a step of obtaining an acetate compound of Chemical Formula 2a by reacting the compound of Chemical Formula 11 obtained in the step as in the presence of a catalyst.

The compound of Chemical Formula 2a can be obtained by reacting the compound of Chemical Formula 11 with red tetraacetate (Pd(OAc)$_4$).

In addition, in the starting material 2 according to the present invention, when A is oxygen (O), as shown in the following Reaction Scheme 3, the compound of Chemical Formula 2, which is the starting material, is prepared by the method comprising: obtaining a lactol compound of Chemical Formula 13 by reacting a compound of Chemical Formula 12 with a reducing agent (Step $b_1$); and obtaining an acetate compound of Chemical Formula 2b by reacting the compound of Chemical Formula 13 obtained in the step $b_1$ with acetic anhydride.

[Reaction Scheme 3]

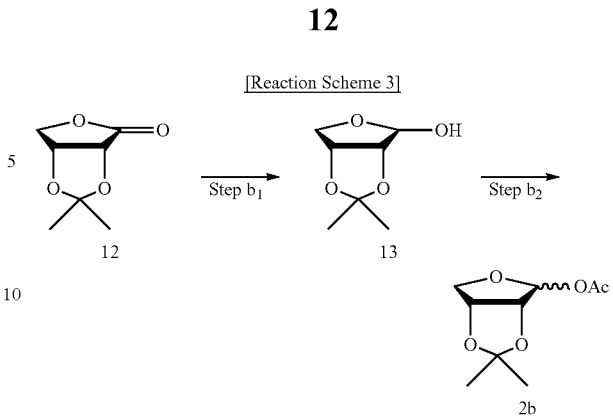

(In the above Reaction Scheme 3, compound 2b is a compound of Chemical Formula 2.)

Hereinafter, another method of preparing the compound of Chemical Formula 2 of the present invention will be described in detail step by step.

Step $b_1$ according to another method of preparing the compound of Chemical Formula 2 of the present invention is a step of obtaining a lactol compound of Chemical Formula 13 by reacting a compound of Chemical Formula 12 with a reducing agent.

The compound of Chemical Formula 13 can be obtained by reducing the compound of Chemical Formula 12 which is easily synthesized, using a diisobutylammonium hydride (DIBAL) catalyst.

Step $b_2$ according to another method of preparing the compound of Chemical Formula 2 of the present invention is a step of obtaining an acetate compound of Chemical Formula 2b by reacting the compound of Chemical Formula 13 obtained in the step $b_1$ with acetic anhydride.

The compound of Chemical Formula 2 can be obtained by reacting the lactol compound of Chemical Formula 13 with acetic anhydride.

In addition, the present invention provides an adenosine $A_3$ antagonist comprising an adenosine derivative represented by the Chemical Formula 1 or a pharmaceutically acceptable salt thereof, as an active ingredient.

Furthermore, the present invention provides a pharmaceutical composition for preventing and treating inflammatory diseases comprising an adenosine derivative represented by the Chemical Formula 1 or a pharmaceutically acceptable salt thereof, as an active ingredient.

When the adenosine $A_3$ receptor is expressed in Chinese hamster ovary (CHO) cells, the $A_3$ receptor has the inhibitory effect of adenylyl cyclase, an enzyme that produces cAMP from ATP, and when the $A_3$ receptor is activated by an agonist, It has been proved that phosphatidylinositol is degraded to activate GTP-dependent phospholipase C, an enzyme that generates inositol phosphate and DAG (Ramkumar, V. et al., J. Biol. Chem., 268, 168871-168890, 1993; Abbacchio, M P et al., Mol. Pharmacol., 48, 1038-1045, 1995). Since this secondary messenger system represents neuronal injury response pathway in cerebral ischemia, such a discovery could explain the response pathway of $A_3$ receptor activation in cerebral ischemia. In addition, adenosine $A_3$ agonists inhibit the release of tumor necrosis factor TNF-$\alpha$, an inflammatory mediator, and the production of inflammatory mediators, MIP-1$\alpha$, interleukin-12 and interferon-$\gamma$, and has protective effect against heart in addition to brain diseases such as epilepsy. In addition, inactivation of the adenosine $A_3$ receptor causes the release of inflammation inducers such as histamine from mast cells, acts to contract the bronchial tubes and induces the apoptosis in immune cells. Thus, adenosine $A_3$ antagonists have potential for development as anti-inflammatory drugs and asthma treatment agents.

In an experiment for measuring the receptor binding affinity so as to evaluate the binding affinity and selectivity of the adenosine derivative of the present invention for the human adenosine receptor (hAR) (see Experimental Example 1), the adenosine derivative of the present invention showed high binding affinity for the human adenosine $A_3$ (h$A_3$ AR) receptor and low affinity for the adenosine $A_1$ and $A_{2A}$ receptors, i.e. high selectivity. In particular, the compound of Example 12 of the present invention exhibited the highest affinity for the h$A_3$ receptor with a $K_i$ value of 1.50±0.40 nM and then the binding affinity is high in order of the compound of Example 2 ($K_i$=1.66±0.90 nM), the compound of Example 14 ($K_i$=2.50±1.00 nM), the compound of Example 10 ($K_i$=3.69±0.25 nM) and the compound of Example 4 ($K_i$=4.16±0.50 nM). The compound of Example 4 of the present invention also showed a high affinity ($K_i$=3.89±1.15 nM) for adenosine $A_3$ receptor in rats expressed in Chinese hamster ovary (CHO) cells. In addition, the compounds of Examples 15 and 16, which are adenosine derivatives having an oxonucleoside form of 4'-O, also showed high binding affinity and selectivity (see Table 1).

In addition, in experiments conducted to investigate the anti-inflammatory activity of the adenosine derivatives of the present invention (see Experimental Examples 3 to 6), it was found that the adenosine derivatives of the present invention have anti-inflammatory activity although this change is small compared to hydrocortisone used as a control group.

Figure 2:
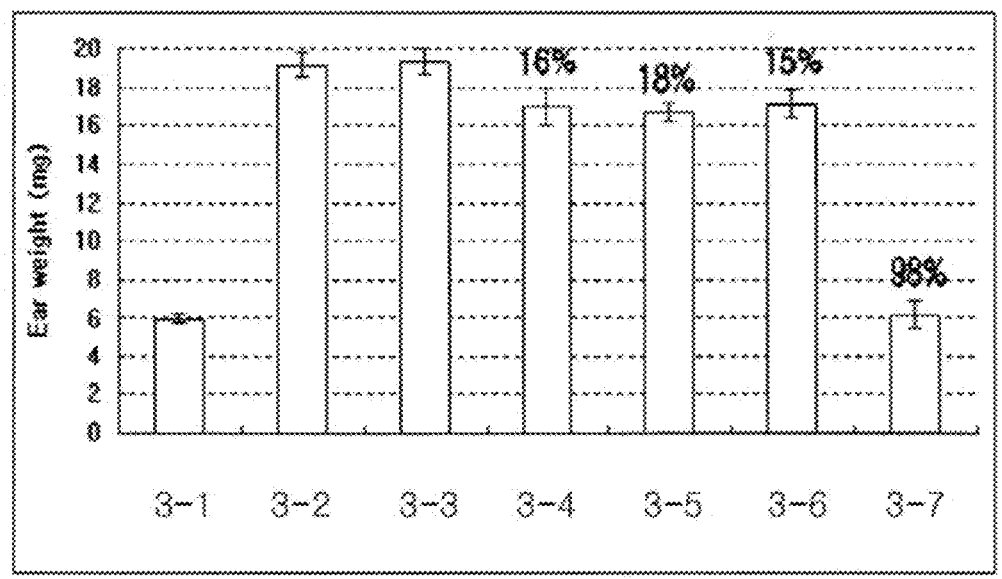
FIG. 2 shows the anti-inflammatory activity of the compounds of the present invention (Examples 2, 3 and 4) by the animal experiments.

From the results of the anti-inflammatory activity after diluting the compounds of Examples 2 to 4 in acetone, it was confirmed that the treatment with compound 4 had an effect of reducing edema for the TPA-induced mouse ear edema (see FIG. 2). In addition, it was found that the measured anti-inflammatory activity of the compounds of Examples 1 and 6 of the present invention after diluting in acetone and treating was 4 times or much higher than that of the compounds of Examples 2 to 4 (see FIG. 3).

Figure 4:
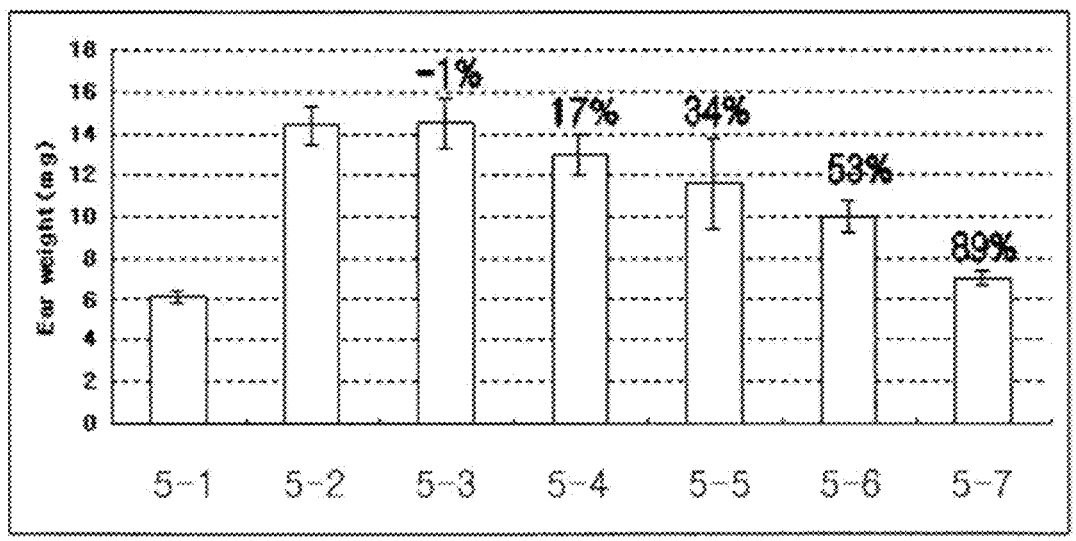
FIG. 4 shows the anti-inflammatory activity of the compounds of the present invention (Examples 5, 7, and 8) by the animal experiments.

The anti-inflammatory activity of the compounds of Examples 5 to 7 of the present invention after diluting to 0.5% in a mixed solvent of distilled water and acetone (1:4) showed inflammation inhibition rates of 17%, 34% and 53%, respectively (See FIG. 4). And the inflammation inhibition rates of the compounds of Examples 15 and 16 after diluting to 0.5% in a mixed solvent of dimethylsulfoxide (DMSO) and acetone (1:9) were 59% and 79%, respectively (See FIG. 5) and it was confirmed that the adenosine derivative compounds of the present invention had anti-inflammatory activity.

Therefore, the adenosine derivatives represented by the Chemical Formula 1 of the present invention show high binding affinity and selectivity for the adenosine $A_3$ receptor, and thus can be effectively used as an excellent adenosine $A_3$ antagonist. In addition, the adenosine derivatives of the present invention antagonize the adenosine $A_3$ receptor and exhibit anti-inflammatory activity, and thus can be used as agent for preventing and treating inflammatory diseases.

In addition, the inflammatory diseases according to the present invention include acute and chronic inflammatory diseases such as alternative inflammation, exudative inflammation, purulent inflammation, hemorrhagic inflammation or proliferative inflammation, etc.

The present invention provides a pharmaceutical composition for preventing or treating eye diseases, which comprises an adenosine derivative comprising a compound represented by the Chemical Formula 1 and/or a pharmaceutically acceptable salt thereof as an active ingredient.

The eye diseases may include all diseases, disorders or symptoms related to the eye such as retinal disease, corneal disease, conjunctival disease, uveal disease, glaucoma, cataract, and the like, and particularly may include intraocular pressure elevation and glaucoma which may be caused from the same or accompanied by such symptoms.

Preferable examples of the adenosine derivatives may be (2R,3R,4S)-2-(2-chloro-6-(3-chlorobenzylamino)-9H-purine-9-yl)tetrahydrothiophene-3,4-diol represented by the above Chemical Formula 1.

[Chemical Formula A]

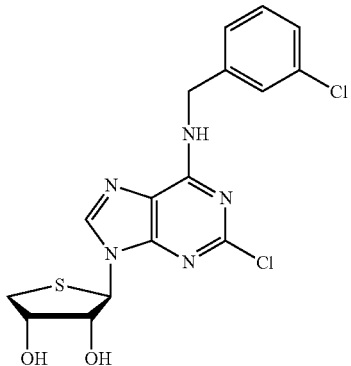

The pharmaceutical composition for preventing and/or treating eye diseases of the present invention can be formulated as an eye drop or an oral administration agent.

The eye drops may comprise the compound represented by the Chemical Formula 1 and/or a pharmaceutically acceptable salt thereof and liquid for eye drops. The liquid for eye drops may include at least one selected from the group consisting of a solubilizer, a viscosity enhancer, an antioxidant, a preservative, and a buffer solution. In an exemplary embodiment, the liquid for eye drops may be a buffer solution at pH 6.8 in which Cremophor EL, glycerin, citric acid and methylparaben are dissolved or mixed.

The oral administration agent may be one in which the compound represented by Chemical Formula 1 and/or a pharmaceutically acceptable salt thereof is formulated into a solid preparation or a liquid preparation.

The solid preparations may be tablets, pills, powders, granules, capsules, and the like and the liquid preparations may be suspensions, solutions, emulsions, syrups and the like, but they are not limited thereto.

The oral administration agent may further comprise an excipient. The excipient may contain at least one selected from the group consisting of methyl cellulose (MC), sucrose, lactose, dimethylsulfoxide (DMSO), polyethylene glycol (PEG), magnesium stearate, calcium carbonate, gelatin, talc, distilled water (DW), liquid paraffin, and the like, and preferably 0.5 wt % of methyl cellulose.

In an exemplary embodiment, the oral administration agent may be a capsule or the like filled with the compound represented by the Chemical Formula 1 and/or a pharmaceutically acceptable salt thereof in a powder state or a solution state dissolved in the above excipient. But it is not limited thereto.

The pharmaceutical composition for preventing and/or treating eye diseases of the present invention can be administered to a patient as an eye drop or an oral preparation through the above-mentioned eye drops or oral administration. However, it is not limited thereto and may be administered by other parenteral administration methods such as intravenous administration and the like.

The adenosine derivatives of the present invention inhibit the production of aqueous humor in the ciliary body and at the same time inhibit the fibrosis in the trabecular meshwork tissue (anti-fibrosis) to exhibit a dual mechanism that promotes the release of aqueous humor (see Examples 11 and 12).

Accordingly, since the intraocular pressure is effectively lowered in a dose-dependent manner (see Experimental Examples 8 to 10), it can be used as a pharmaceutical composition which is highly suitable for preventing and/or treating eye diseases such as glaucoma.

In addition, since the adenosine derivative of the present invention exhibits physicochemical properties suitable for oral administration (see Experimental Example 13), excellent in blood concentration and stability at the time of oral administration (see Examples 14 to 18), is a biocompatible substance with little toxicity in the body (See Experimental Example 19), and excellent in storage stability when formulated as an oral administration agent (see Experimental Example 20), it can be used as an very effective active ingredient for oral administration for preventing and/or treating eye diseases.

EXAMPLE

Preparation of Starting Material

<Preparation Example 1> Preparation of (3aR,4R,6aS)-2,2-dimethyltetrahydrothieno[3,4-d][1,3]dioxol-4-yl acetate Step $a_1$. Preparation of (3aR,4R,6R,6aR)-6-(2,2-dimethyl-1,3-dioxolane-4-yl)-2,2-dimethyl-tetrahydrofuro[3,4-d][1,3]dioxol-4-ol D-mannose (1.74 g, 6.52 mmol) and 2,2-dimethoxypropane (2.45 ml, 19.55 mmol) were added to acetone (50 ml), stirred and cooled to 0° C. Concentrated sulfuric acid (0.45 g, 1.96 mmol) was added dropwise to it. The reaction mixture was stirred at room temperature for 24 hours. Triethylamine was added to the mixture for neutralization, and the mixture was concentrated under reduced pressure. The mixture obtained after concentration was subjected to silica gel column chromatography using a hexane:ethyl acetate mixed solvent (1:1, v/v) as an eluent to obtain the target compound as a white solid (1.61 g, 95%).

mp 120.3-120.5° C.;
$^1$H-NMR (CDCl$_3$) δ 5.34 (s, 1H), 4.76-4.79 (m, 1H), 4.58 (d, 1H, J=6.0 Hz), 4.34-4.39 (m, 1H), 4.15 (dd, 1H, J=3.6, 7.2 Hz), 4.00-4.08 (m, 2H);
$[α]^{25}_D$ 11.71 (c 0.11, CH$_2$Cl$_2$); FAB-MS m/z 261 [M+H]$^+$.

Step $a_2$. Preparation of (1R)-(2,2-dimethyl-1,3-dioxolane-4-yl)((4R,5S)-5-(hydroxymethyl)-2,2-dimethyl-1,3-dioxolane-4-yl) methanol To ethanol (25 ml), (3aR,4R,6R,6aR)-6-(2,2-dimethyl-1,3-dioxolane-4-yl)-2,2-tetrahydrofuro[3,4-d][1,3]dioxol-4-01 (1.50 g, 5.76 mmol) prepared in the step $a_1$ was carefully divided and added and cooled to 0° C. Sodium borohydride (NaHB$_4$, 440 mg, 11.53 mmol) was added thereto and stirred at room temperature for 2 hours. The reaction mixture was neutralized with acetic acid and then concentrated under reduced pressure. The mixture was extracted with ethyl acetate and water, and then the organic layer was dried over anhydrous magnesium sulfate (MgSO$_4$), filtered, and then concentrated under reduced pressure. The mixture obtained after concentration was subjected to silica gel column chromatography using a hexane:ethyl acetate mixed solvent (1:1, v/v) as an eluent to obtain the target compound in the form of a syrup (1.38 g, 92%).

$^1$H-NMR (CDCl$_3$) δ 4.33 (dd, 1H, J=1.6, 7.2 Hz), 4.24-4.28 (m, 1H), 4.06-4.13 (m, 2H), 3.92-3.97 (m, 1H), 3.76-3.85 (m, 2H), 3.59-3.61 (m, 1H), 1.48 (s, 3H), 1.38 (s, 3H), 1.36 (s, 3H), 1.33 (s, 3H);
$[α]^{25}_D$-3.88 (c 0.44, CH$_2$Cl$_2$);
FAB-MS m/z 263 [M+H]$^+$.

Step $a_3$. Preparation of (1R)-(2,2-dimethyl-1,3-dioxolane-4-yl)((4S,5S)-2,2-dimethyl-5-((methylsulfonyloxy)methyl)-1,3-dioxolane-4-yl)methyl methanesulfonate To a mixture of dichloromethane (300 ml) and triethylamine (163.75 ml, 1.17 mol), (1R)-(2,2-dimethyl-1,3-dioxolane-((4R,5S)-5-(hydroxymethyl)-2,2-dimethyl-1,3-dioxolan-4-yl)methanol (38.52 g, 146.85 mmol) prepared in the step $a_2$ and 4-dimethylaminopyridine (4-DMAP, 5.38 mg, 44.06 mmol) were added and mixed and cooled to 0° C. Dimethanesulfonyl chloride (47.59 mL, 587.42 mmol) was added dropwise carefully thereto. After stirring for 1 hour at room temperature, the reaction mixture was extracted with dichloromethane and washed with saturated aqueous sodium bicarbonate (NaHCO$_3$). The organic layer was collected and dried over anhydrous magnesium sulfate (MgSO$_4$), filtered and then concentrated under reduced pressure. Dimesyl compound in the form of brown syrup obtained by concentration was subjected to silica gel column chromatography using a hexane:ethyl acetate mixed solvent (5:1, v/v) as an eluent to obtain the target compound in the form of a syrup (57.83 g, 94%).

$^1$H-NMR (CDCl$_3$) δ 4.75 (pseudo t, 1H, J=7.4 Hz), 4.33-4.45 (m, 4H), 4.06-4.20 (m, 3H), 3.12 (s, 3H), 3.07 (s, 3H), 1.51 (s, 3H), 1.43 (s, 3H), 1.37 (s, 3H), 1.33 (s, 3H);
$[α]^{25}_D$ 38.32 (c 0.29, CH$_2$Cl$_2$);
FAB-MS m/z 419 [M+H]$^+$.

Step $a_4$. Preparation of (3aR,4S,6aS)-4-(2,2-dimethyl-1,3-dioxolane-4-yl)-2,2-dimethyltetrahydrothieno[3,4-d][1,3]dioxol (1R)-(2,2-dimethyl-1,3-dioxolane-4-yl)((4S,5S)-2,2-dimethyl-5-(methylsulfonyloxy)methyl-1,3-dioxolan-4-yl) methylmethanesulfonate (993.80 g, 2.23 mmol) prepared in the step as was dissolved into DMF (50 ml) and sodium sulfide (348.30 g, 4.46 mmol) was added thereto and the mixture was then refluxed and stirred at 80° C. overnight. After completion of the reaction, the solvent was removed under reduced pressure and the residue was extracted with ethyl acetate and water. The organic layer was dried over anhydrous magnesium sulfate (MgSO$_4$), filtered, and then concentrated under reduced pressure. The residue obtained after concentration was subjected to silica gel column chromatography using a hexane:ethyl acetate mixed solvent (8:1, v/v) as an eluent to obtain a target compound in the form of a syrup (453.0 mg, 78%).

¹H-NMR (CDCl₃) δ 4.92 (dt, 1H, J=1.8, 5.6 Hz), 4.72 (dd, 1H, J=2.0, 6.0 Hz), 4.26-4.30 (m, 1H), 4.04 (s, 1H), 3.79 (t, 1H, J=3.8 Hz), 3.31-3.32 (m, 1H), 3.19 (dd, 1H, J=5.4, 12.0 Hz), 2.84 (dd, 1H, J=1.6, 12.0 Hz), 1.51 (s, 3H), 1.43 (s, 3H), 1.32 (dd, 6H, J=8.4 Hz);

$[\alpha]_D^{25}$-96.04 (c 0.20, $CH_2Cl_2$);

FAB-MS m/z 261 $[M+H]^+$.

Step a₅. Preparation of 1-((3aR,4S,6aS)-2,2-dimethyltetrahydrothieno[3,4-d][1,3]dioxol-4-yl) ethane-1,2-diol (3aR,4S,6aS)-4-(2,2-dimethyl-1,3-dioxolan-4-yl)-2,2-dimethyltetrahydrothieno[3,4-d][1,3]dioxol (21.78 g, 83.66 mmol) prepared in the step a₄ was dissolved in a 60% aqueous acetic acid solution (250 ml) and stirred at room temperature for 2 hours. The reaction mixture was concentrated under reduced pressure and the resulting residue was subjected to silica gel column chromatography using a hexane:ethyl acetate mixed solvent (1:2, v/v) as an eluent to obtain the target compound as a white solid (14.85 g, 81%).

¹H-NMR (CDCl₃) δ 4.92 (dt, 1H, J=1.8, 5.6 Hz), 4.72 (dd, 1H, J=2.0, 6.0 Hz), 4.26-4.30 (m, 1H), 4.04 (s, 1H), 3.79 (t, 1H, J=3.8 Hz), 3.31-3.32 (m, 1H), 3.19 (dd, 1H, J=5.4, 12.0 Hz), 2.84 (dd, 1H, J=1.6, 12.0 Hz), 1.51 (s, 3H), 1.43 (s, 3H), 1.32 (dd, 6H, J=8.4 Hz);

$[\alpha]_D^{25}$-96.04 (c 0.20, $CH_2Cl_2$);

FAB-MS m/z 261 $[M+H]^+$.

Step a₆. Preparation of (3aR,4R,6aS)-2,2-dimethyltetrahydrothieno[3,4-d][1,3]dioxol-4-yl acetate 1-((3aR,4S,6aS)-2,2-dimethyltetrahydrothieno[3,4-d][1,3]dioxol-4-yl)ethane-1,2-diol (14.85 g, 67.41 mmol) prepared in the step a₅ was dissolved in ethylacetate (300 ml) and cooled to 0° C. Red tetraacetate (Pb(OAc)₄, 157.31 g, 337.06 mmol) was added thereto and stirred at room temperature overnight. The reaction mixture was filtered through celite and the filtrate was diluted with ethyl acetate. The organic layer was diluted with dichloromethane, washed with saturated aqueous sodium bicarbonate (NaHCO₃), dried over anhydrous magnesium sulfate, and concentrated under reduced pressure. The residue obtained after concentration was subjected to silica gel column chromatography using a hexane:ethyl acetate mixed solvent (8:1, v/v) as an eluent to obtain the target compound in the form of a syrup (8.82 g, 60%).

¹H-NMR (CDCl₃) δ 5.03 (dd, 1H, J=5.6, 9.6 Hz), 4.79 (dd, 1H, J=5.6, 8.8 Hz), 3.21-3.27 (m, 2H), 3.01 (dt, 2H, J=0.8, 12.8 Hz), 2.05 (s, 3H), 1.50 (s, 3H), 1.31 (s, 3H);

$[\alpha]_D^{25}$-258.15 (c 0.18, $CH_2Cl_2$);

FAB-MS m/z 218 $[M]^+$.

<Preparation Example 2> Preparation of (3aS,4S,6aS)-2,2-dimethyl-tetrahydrofuro[3,4-d][1,3]dioxol-4-yl acetate Step b₁. Preparation of (3aR,4R,6aR)-2,2-dimethyltetrahydrofuro[3,4-d][1,3]dioxol-4-ol After dissolving 2,3-O-isopropylidene-D-erythronolactone (1.04 g, 6.42 mmol) in toluene (20 mL), 1 M diisobutylammonium hydride (DIBAL)/THF solution was added at −78° C. The reaction mixture was stirred at the same temperature for 30 minutes and then the reaction was terminated by adding methanol slowly. The suspension was filtered through celite, extracted with ethyl acetate and water, and then subjected to silica gel column chromatography using a hexane:ethyl acetate mixed solvent (3:1, v/v) as an eluent to obtain the target compound in the form of a syrup (1.94 g, 96%).

¹H-NMR (CDCl₃) δ 5.39 (s, 1H), 4.82 (dd, 1H, J=3.6, 6.0 Hz), 4.55 (d, 1H, J=6.0 Hz), 4.05 (dd, 1H, J=3.6, 10.2 Hz), 4.00 (d, 1H, J=10.0 Hz), 1.45 (s, 3H), 1.30 (s, 3H).

Step b₂. Preparation of (3aS,4S,6aS)-2,2-dimethyltetrahydrofuro[3,4-d][1,3]dioxol-4-yl acetate After dissolving the lactol compound (875.9 mg, 5.47 mmol) prepared in the step b₁ of Preparation Example 2 in pyridine (10 mL), acetic anhydride (0.67 mL, 6.56 mmol) was added at 0° C. The reaction mixture was stirred at room temperature for 3 hours and then concentrated under reduced pressure. After concentration, the residue was extracted with ethyl acetate and water, and then the organic layer was dried over anhydrous magnesium sulfate and concentrated under reduced pressure. The residue was subjected to silica gel column chromatography using a hexane:ethyl acetate mixed solvent (8:1, v/v) as an eluent to obtain the target compound in the form of a syrup (702.1 mg, 65%).

¹H-NMR (CDCl₃) δ 6.16 (s, 1H), 4.86 (dd, 1H, J=3.6, 6.0 Hz), 4.66 (d, 1H, J=6.0 Hz), 4.12 (d, 1H, J=6.4 Hz), 3.99 (dd, 1H, J=3.6, 10.8 Hz), 2.05 (s, 3H), 1.48 (s, 3H), 1.33 (s, 3H).

<Example 1> Preparation of (2R,3R,4S)-2-(2-chloro-6-(3-fluorobenzylamino)-9H-purin-9-yl)tetrahydrothiophene-3,4-diol Step 1. Preparation of 2,6-dichloro-9-((3aR,4R,6aS)-2,2-dimethyltetrahydrothieno [3,4-d][1,3]dioxol-4-yl)-9H-purine After dissolving 2,6-dichloropurine (2.29 g, 22.12 mmol) and ammonium sulfate (438 mg, 3.32 mmol) in hexamethyldisilazane (HMDS, 50 mL), it was refluxed overnight in an inert and dry condition. The reaction mixture was concentrated under reduced pressure and the resulting solid mixture was redissolved in cold 1,2-dichloroethane (20 mL). (3aR,4R,6aS)-2,2-dimethyltetrahydrothieno[3,4-d][1,3]dioxol-4-yl acetate (1.41 g, 11.06 mmol) obtained in Preparation Example 1 was dissolved in 1,2-dichloroethane (20 ml) and added dropwise again to the above solution. Trimethylsilyltrifluoromethanesulfonate (TMSOTf, 4.0 ml, 22.12 mmol) was added dropwise to the mixture and stirred at 0° C. for 30 minutes, then at room temperature for 1 hour and then heated to 80° C. and stirred for 2 hours. The reaction mixture was cooled, diluted with dichloromethane and washed with saturated aqueous sodium bicarbonate (NaHCO₃). The organic layer was dried over anhydrous magnesium sulfate (MgSO₄) and concentrated under reduced pressure to obtain a yellow syrupy residue. The residue was subjected to silica gel column chromatography using a mixed solvent of dichloromethane and methanol (50:1, v/v) as an eluent to obtain the compound in the form of foam (3.03 g, 79%).

UV ($CH_2Cl_2$)$\lambda_{max}$ 275.0 nm;

¹H-NMR (CDCl₃) δ 8.17 (s, 1H), 5.87 (s, 1H), 5.32 (pseudo t, 1H, J=4.8 Hz), 5.21 (d, 1H, J=5.6 Hz), 3.79 (dd, 1H, J=4.4, 12.8 Hz), 3.26 (d, 1H, J=13.2 Hz), 1.59 (s, 3H), 1.36 (s, 3H);

$[\alpha]_D^{25}$-42.04 (c 0.16, $CH_2Cl_2$);

FAB-MS m/z 347 $[M+H]^+$.

Step 2. Preparation of (2R,3S,4S)-2-(2,6-dichloro-9H-purin-9-yl)tetrahydrothiophene-3,4-diol After dissolving 2,6-dichloro-9-((3aR,4R,6aS)-2,2-dimethyltetrahydrothieno[3,4-d][1,3]dioxol-4-yl)-9H-purine prepared in the step 1 in tetrahydrofuran (20 ml), 2 N hydrochloric acid was added and stirred overnight at room temperature. The mixture was neutralized with 1 N aqueous sodium hydroxide solution and then carefully concentrated under reduced pressure. The residue after concentration was subjected to silica gel column chromatography using a dichloromethane:methanol mixed solvent (20:1', v/v) as am eluent to obtain the target compound as a white solid (1.94 g, 96%).

mp 198.3-200.3° C.;
UV (MeOH) $\lambda_{max}$ 275.0 nm;
$^1$H-NMR (CD$_3$OD) δ 8.87 (s, 1H), 6.08 (d, 1H, J=6.8 Hz), 4.69 (q, 1H, J=3.2 Hz), 4.48 (q, 1H, J=3.6 Hz), 3.56 (dd, 1H, J=4.4, 11.2 Hz), 2.97 (dd, 1H, J=3.4, 11.2 Hz);
$[\alpha]^{25}_D$-50.43 (c 0.12, DMSO);
FAB-MS m/z 307 [M+H]$^-$.

Step 3. Preparation of (2R,3R,4S)-2-(2-chloro-6-(3-fluorobenzylamino)-9H-purin-9-yl) tetrahydrothiophene-3,4-diol After dissolving (2R,3S,4S)-2-(2,6-dichloro-9H-purin-9-yl)tetrahydrothiophene-3,4-diol (1 eq.) prepared in the step 2 and 3-fluorobenzylamine (1.5 eq.) in ethanol (5 ml) at room temperature, the reaction mixture was stirred at room temperature for 2-3 h. After completion of the reaction, the residue obtained by concentration under reduced pressure was subjected to silica gel column chromatography using a dichloromethane:methanol mixed solvent (20:1, v/v) as an eluent to obtain the target compound (0.10 g, 80%). mp 183.2-183.5° C.;

UV (MeOH) $\lambda_{max}$ 275.0 nm;
$^1$H-NMR (DMSO-d$_6$) δ 8.91 (t, 1H—NH, J=5.8 Hz), 8.51 (s, 1H), 7.33-7.39 (m, 1H), 7.13-7.18 (m, 2H), 7.06 (dt, 1H, J=2.8, 11.6 Hz), 5.82 (d, 1H, J=7.2 Hz), 5.56 (d, 1 H—OH, J=6.0 Hz), 5.37 (d, 1H—OH, J=4.4 Hz), 4.65 (d, 1H, J=6.0 Hz), 4.60 (m, 1H), 4.33-4.35 (m, 1H), 3.41 (dd, 1H, J=4.0, 10.8 Hz), 2.79 (dd, 1H, J=2.8, 10.8 Hz);
$[\alpha]^{25}_D$-96.21 (c 0.12, DMSO);
FAB-MS m/z 396 [M+H]$^+$.

<Example 2> Preparation of (2R,3R,4S)-2-(2-chloro-6-(3-chlorobenzylamino)-9H-purin-9-yl)tetrahydrothiophene-3,4-diol Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in step 2 of the Example 1.

Step 3. Preparation of (2R,3R,4S)-2-(2-chloro-6-(3-chlorobenzylamino)-9H-purin-9-yl)tetrahydrothiophene-3,4-diol The synthesis was conducted under the same conditions as in the step 3 of the Example 1 using 3-chlorobenzylamine instead of 3-fluorobenzylamine to obtain the target compound (0.11 g, 83%).

mp 163.3-165.3° C.;
UV (MeOH) $\lambda_{max}$ 274.5 nm;
$^1$H-NMR (CD$_3$OD) δ 8.34 (s, 1H), 7.41 (s, 1H), 7.24-7.34 (m, 3H), 5.94 (d, 1H, J=6.4 Hz), 4.75 (brs, 2H), 4.61 (q, 1H, J=3.2 Hz), 4.45 (q, 1H, J=4.0 Hz), 3.51 (dd, 1H, J=4.8, 11.2 Hz), 2.95 (dd, 1H, J=3.6, 10.8 Hz);
FAB-MS m/z 411 [M]$^+$.

<Example 3> Preparation of (2R,3R,4S)-2-(2-chloro-6-(3-bromobenzylamino)-9H-purin-9-yl)tetrahydrothiophene-3,4-diol Step 1. Preparation of 2,6-dichloro-9-((3aR,4R,6aS)-2,2-dimethyltetrahydrothieno [3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of (2R,3R,4S)-2-(2-chloro-6-(3-bromobenzylamino)-9H-purin-9-yl)tetrahydrothiophene-3,4-diol The synthesis was conducted under the same conditions as in the step 3 of Example 1 using 3-bromobenzylamine instead of 3-fluorobenzylamine to obtain the target compound (0.12 g, 83%).

mp 184.0-185.0° C.;
UV (MeOH) $\lambda_{max}$ 274.0 nm;
$^1$H-NMR (DMSO-d$_6$) δ 8.91 (brs, 1H—NH), 8.51 (s, 1H), 7.55 (s, 1H), 7.43 (d, 1H, J=7.6 Hz), 7.33-7.35 (m, 1H), 7.26-7.30 (m, 1H), 5.82 (d, 1H, J=7.2 Hz), 5.57 (d, 1H—OH, J=6.0 Hz), 5.38 (d, 1H—OH, J=4.0 Hz), 4.60-4.63 (m, 3H), 4.34 (s, 1H), 3.41 (dd, 1H, J=4.4, 11.2 Hz), 2.80 (dd, 1H, J=2.8, 10.8 Hz);
FAB-MS m/z 456 [M+H]$^+$.

<Example 4> Preparation of (2R,3R,4S)-2-(2-chloro-6-(3-iodobenzylamino)-9H-purin-9-yl)tetrahydrothiophene-3,4-diol Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of (2R,3R,4S)-2-(2-chloro-6-(3-iodobenzylamino)-9H-purin-9-yl)tetrahydrothiophene-3,4-diol The synthesis was conducted under the same conditions as in the step 3 of Example 1 by using 3-iodobenzylamine instead of 3-fluorobenzylamine to obtain the target compound (0.14 g, 84%).

mp 198.7-199.9° C.;
UV (MeOH) $\lambda_{max}$ 274.0 nm;
$^1$H-NMR (DMSO-d$_6$) δ 8.90 (t, 1H—NH, J=6.4 Hz), 8.51 (s, 1H), 7.74 (s, 1H), 7.60 (d, 1H, J=7.6 Hz), 7.35 (d, 1H, J=7.6 Hz), 7.13 (t, 1H, J=8.0 Hz), 5.82 (d, 1H, J=7.6 Hz), 5.56 (d, 1H, J=6.4 Hz), 5.37 (d, 1H, J=4.0 Hz), 4.60 (d, 3H, J=4.4 Hz), 4.34 (brs, 1H), 3.38 (dd, 1H, J=4.0, 10.8 Hz), 2.80 (dd, 1H, J=4.0, 10.8 Hz);
$[α]^{25}_D$-78.91 (c 0.13, DMSO);
FAB-MS m/z 504 [M+H]$^+$.

<Example 5> Preparation of (2R,3R,4S)-2-(2-chloro-6-(2-chlorobenzylamino)-9H-purin-9-yl) tetrahydrothiophene-3,4-diol Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl) tetrahydrothiophene-3,4-diol The target compound as a white solid was obtained in the same manner as in the step 2 of the Example 1.

Step 3. Preparation of (2R,3R,4S)-2-(2-chloro-6-(2-chlorobenzylamino)-9H-purin-9-yl)tetrahydrothiophene-3,4-diol The synthesis was conducted under the same conditions as in the step 3 of the Example 1 by using 2-chlorobenzylamine instead of 3-fluorobenzylamine to obtain the target compound (0.11 g, 81%).
mp 198.7-199.7° C.;
UV (MeOH)$\lambda_{max}$ 273.5 nm;
$^1$H-NMR (CD$_3$OD) δ 8.35 (brs, 1H), 7.45-7.47 (m, 1H), 7.39-7.43 (m, 1H), 7.25-7.29 (m, 2H), 5.95 (d, 1H, J=6.4 Hz), 4.60-4.63 (m, 1H), 4.45 (dd, 1H, J=3.6, 8.0 Hz), 3.51 (dd, 1H, J=4.8, 10.8 Hz), 2.95 (dd, 1H, J=4.0, 10.8 Hz);
$[α]^{25}_D$-96.21 (c 0.12, DMSO);
FAB-MS m/z 412 [M+H]$^+$.

<Example 6> Preparation of (2R,3R,4S)-2-(2-chloro-6-(5-chloro-2-methoxybenzylamino)-9H-purin-9-yl)tetrahydrothiophene-3,4-diol Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of (2R,3R,4S)-2-(2-chloro-6-(5-chloro-2-methoxybenzylamino)-9H-purin-9-yl)tetrahydrothiophene-3,4-diol The synthesis was carried out under the same conditions as in the step 3 of the Example 1 by using 5-chloro-2-methoxybenzylamine instead of 3-fluorobenzylamine to obtain the target compound (0.11 g, 78%).
mp 188.8-189.8° C.;
UV (MeOH) $\lambda_{max}$ 275.5 nm;
$^1$H-NMR (DMSO-d$_6$) δ 8.64 (t, 1H—NH, J=6.0 Hz), 8.51 (s, 1H), 7.21-7.25 (m, 1H), 7.12 (d, 1H, J=7.2 Hz), 7.00 (d, 1H, J=8.0 Hz), 6.85-6.89 (m, 1H), 5.82 (d, 1H, J=7.6 Hz), 5.57 (d, 1H—OH, J=6.4 Hz), 5.37 (d, 1H—OH, J=4.0 Hz), 4.61-4.63 (m, 2H), 4.35 (m, 1H), 3.84 (s, 3H), 3.71 (dd, 1H, J=3.6, 10.4 Hz), 2.80 (dd, 1H, J=2, 4, 10.8 Hz);
$[α]^{25}_D$-96.10 (c 0.21, DMSO);
FAB-MS m/z 442 [M+H]$^+$.

<Example 7> Preparation of (2R,3R,4S)-2-(2-chloro-6-(2-methoxybenzylamino)-9H-purin-9-yl) tetrahydrothiophene-3,4-diol Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of (2R,3R,4S)-2-(2-chloro-6-(2-methoxybenzylamino)-9H-purin-9-yl)tetrahydrothiophene-3,4-diol The synthesis was conducted under the same conditions as in the step 3 of the Example 1 by using 2-methoxybenzylamine instead of 3-fluorobenzylamine to obtain the target compound (0.12 g, 88%).
mp 188.0° C.;
UV (MeOH) $\lambda_{max}$ 276.5 nm;
$^1$H-NMR (DMSO-d$_6$) δ 8.65 (t, 1H—NH, J=6.0 Hz), 8.51 (s, 1H), 7.21-7.25 (m, 1H), 7.12 (d, 1H, J=7.2 Hz), 7.00 (d, 1H, J=8.0 Hz), 6.85-6.89 (m, 1H), 5.83 (d, 1H, J=6.8 Hz), 5.58 (d, 1H—OH, J=6.4 Hz), 5.39 (d, 1H—OH, J=3.6 Hz), 4.62-4.64 (m, 2H), 4.35 (s, 1H), 3.84 (s, 1H), 3.42 (dd, 1H, J=3.6, 10.4 Hz), 2.79-2.82 (m, 1H);
$[α]^{25}_D$-93.53 (c 0.17, DMSO);
FAB-MS m/z 407 [M+H]$^+$.

<Example 8> Preparation of (2R,3R,4S)-2-(2-chloro-6-(naphthalen-1-ylmethylbenzylamino)-9H-purin-9-yl)tetrahydrothiophene-3,4-diol Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of (2R,3R,4S)-2-(2-chloro-6-(naphthalen-1-ylmethylbenzylamino)-9H-purin-9-yl)tetrahydrothiophene-3,4-diol The synthesis was conducted under the same conditions as in the step 3 of the Example 1 by using naphthalene-1-ylmethylbenzylamine instead of 3-fluorobenzylamine to obtain the target compound (0.13 g, 90%).

mp 226.3° C. (decomp);
UV (MeOH) $\lambda_{max}$ 281.0 nm;
$^1$H-NMR (DMSO-d$_6$) δ 8.96 (t, 1H—NH, J=6.0 Hz), 8.51 (s, 1H), 8.25 (d, 1H, J=8.0 Hz), 7.95-7.97 (m, 1H), 7.83-7.85 (m, 1H), 7.53-7.61 (m, 2H), 7.43-7.46 (m, 2H), 5.82 (d, 1H, J=7.6 Hz), 5.56 (d, 1H, J=6.4 Hz), 5.38 (d, 1H, J=4.0 Hz), 5.12 (d, 1H, J=6.0 Hz), 4.59-4.61 (m, 1H), 4.34-4.35 (m, 1H), 3.40-3.44 (m, 1H), 2.80 (dd, 1H, J=2.4, 6.8 Hz);
FAB-MS m/z 428 [M+H]$^+$.

<Example 9> Preparation of 3-((2-chloro-9-((2R,3S,4R)-3,4-dihydroxytetrahydrothiophen-2-yl)-9H-purin-6-ylamino)methyl)benzoic acid

Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of 3-((2-chloro-9-((2R,3S,4R)-3,4-dihydroxytetrahydrothiophen-2-yl)-9H-purin-6-ylamino)methyl)benzoic acid The synthesis was conducted under the same conditions as in the step 3 of the Example 1 by using 3-(aminomethyl)benzoic acid instead of 3-fluorobenzylamine to obtain the target compound (0.12 g, 84%).

mp 254.0-256.9° C.;
UV (MeOH) $\lambda_{max}$ 275.5 nm;
$^1$H-NMR (DMSO-d$_6$) δ 8.95 (t, 1H—NH, J=6.0 Hz), 8.52 (s, 1H), 7.89 (d, 1H, J=8.4 Hz), 7.43 (d, 1H, J=8.0 Hz), 5.82 (d, 1H, J=7.6 Hz), 5.57 (brs, 1H), 5.38 (brs, 1H), 4.71 (d, 1H, J=6.0 Hz), 4.60 (brs, 1H), 4.34 (brs, 1H), 3.41 (dd, 1H, J=4.0, 10.8 Hz), 2.80 (dd, 1H, J=2.8, 10.8 Hz);
$[\alpha]^{25}_D$-94.55 (c 0.11, DMSO);
FAB-MS m/z 422 [M+H]$^+$.

<Example 10> Preparation of 2-(2-chloro-6-methylamino-purin-9-yl)(2R,3S,4R)-tetrahydrothiophene-3,4-diol

Step 1. Preparation of 2,6-dichloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 1.

Step 2. Preparation of (2R,3S,4S)-2-(2,6-dichloro-9H-purin-9-yl)tetrahydrothiophene-3,4-diol The target compound as a white solid was obtained in the same manner as in the step 2 of the Example 1.

Step 3. Preparation of 2-(2-chloro-6-methylamino-purin-9-yl)(2R,3S,4R)-tetrahydrothiophene-3,4-diol The synthesis was conducted under the same conditions as in the step 3 of the Example 1 by using methylamine instead of 3-fluorobenzylamine to obtain the target compound (0.89 g, 90%).

UV (MeOH) $\lambda_{max}$ 269.5 nm (pH 7);
$^1$H-NMR (CDCl$_3$) δ 2.99 (1H, dd, 4'-CH, J=4.4, 10.8 Hz), 3.12 (3H, brs, NH—CH$_3$), 3.44 1H, dd, 4'-CH, J=4, 10.8 Hz), 4.41 (1H, m, 2'-CH, J=5.6 Hz), 4.47 (1H, m, 3'-CH), 5.89 (1H, d, 1'-CH, J=5.6 Hz), 8.40 (s, 1H, 8-CH);
$[\alpha]^{25}_D$-34.8 (c 0.115, DMSO);
FAB-MS m/z 302.3 [M+H]$^+$.

<Example 11> Preparation of (2R,3R,4S)-2-(6-(3-fluorobenzylamino)-9H-purin-9-yl) tetrahydrothiophene-3,4-diol

Step 1. Preparation of 6-chloro-9-((3aR,4R,6aS)-2,2-dimethyltetrahydrothieno [3,4-d][1,3]dioxol-4-yl)-9H-purine The synthesis was conducted under the same conditions as in the step 1 of the Example 1 by using 6-chloropurine (2.29 g, 22.12 mmol) instead of 2,6-chloropurine to obtain the target compound in the form of foam (1.84 g, 91%).

UV (CH$_2$Cl$_2$)$\lambda_{max}$ 265.0 nm;
$^1$H-NMR (CDCl$_3$) δ 8.67 (pseudo t, 1H, J=1.4 Hz), 8.23 (s, 1H), 5.88 (s, 1H), 5.23 (m, 2H), 3.69 (dd, 1H, J=4.0, 13.2 Hz), 3.18 (d, 1H, J=12.8 Hz), 1.52 (s, 3H), 1.29 (s, 3H);
$^{13}$C-NMR (CDCl$_3$) δ 152.05, 151.39, 151.09, 144.34, 132.56, 111.90, 89.60, 84.31, 70.30, 40.76, 26.40, 24.63;
$[\alpha]^{25}_D$-157.64 (c 0.15, MeOH);
FAB-MS m/z 313 [M+H]$^+$.

Step 2. Preparation of (2R,3S,4S)-2-(6-chloro-9H-purin-9-yl)tetrahydrothiophene-3,4-diol The synthesis was conducted by using 6-chloro-9-((3aR,4R,6aS)-2,2-dimethyltetrahydrothieno[3,4-d][1,3]dioxol-4-yl)-9H-purine (1.84 g, 5.88 mmol) prepared in the step 1 under the same conditions as in the step 2 of the Example 1 to obtain the target compound as a white solid (1.27 g, 79%).

mp 192.3-192.8° C.;
UV (MeOH) $\lambda_{max}$ 264.5 nm;
$^1$H-NMR (DMSO-d$_6$) δ 9.02 (s, 1H), 8.82 (s, 1H), 6.02 (d, 1H, J=7.6 Hz), 5.62 (d, 1H—OH, J=6.0 Hz), 5.43 (d, 1H—OH, J=4.0 Hz), 4.70-4.74 (m, 1H), 4.36-4.40 (m, 1H), 3.47 (dd, 1H, J=4.0, 10.8 Hz), 3.17 (d, 1H, J=5.2 Hz), 2.84 (dd, 1H, J=2.8, 11.2 Hz);
$[\alpha]^{25}_D$-109.15 (c 0.16, DMSO);
FAB-MS m/z 273 [M+H]$^+$.

Step 3. Preparation of (2R,3R,4S)-2-(6-(3-fluorobenzylamino)-9H-purin-9-yl)tetrahydrothiophene-3,4-diol After dissolving (2R,3S,4S)-2-(6-chloro-9H-purin-9-yl)tetrahydrothiophene-3,4-diol (1 eq.) prepared in the step 2 and 3-fluorobenzylamine (1.5 eq.) in ethanol (5 ml) at room temperature, the reaction mixture was stirred at room temperature for 2 to 3 hours. After completion of the reaction, the reaction mixture was concentrated under reduced pressure, and the residue was subjected to silica gel column chromatography using a dichloromethane:methanol mixed solvent (20:1, v/v) as an eluent to obtain the target compound (0.11 g, 82%).

mp 180.5-180.7° C.;

UV (MeOH) $\lambda_{max}$ 273.5 nm;

$^1$H-NMR (DMSO-d$_6$) δ 8.46 (s, 1H), 8.22 (s, 1H), 7.31-7.39 (m, 1H), 7.12-7.18 (m, 2H), 7.01-7.05 (m, 1H), 5.90 (d, 1H, J=7.2 Hz), 5.53 (d, 1H—OH, J=6.4 Hz), 5.35 (d, 1H—OH, J=4.0 Hz), 4.67-4.71 (m, 2H), 4.35-4.37 (m, 1H), 3.39-3.43 (m, 1H), 3.17 (d, 1H, J=5.2 Hz), 2.80 (dd, 1H, J=3.2, 11.2 Hz);

$[α]^{25}_D$-141.2 (c 0.11, DMSO);

FAB-MS m/z 362 [M+H]$^+$.

<Example 12> Preparation of (2R,3R,4S)-2-(6-(3-chlorobenzylamino)-9H-purin-9-yl)tetrahydrothiophene-3,4-diol Step 1. Preparation of 6-chloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 11.

Step 2. Preparation of (2R,3S,4S)-2-(6-chloro-9H-purin-9-yl) tetrahydrothiophene-3,4-diol The target compound as a white solid was obtained in the same manner as in the step 2 of the Example 11.

Step 3. Preparation of (2R,3R,4S)-2-(6-(3-chlorobenzylamino)-9H-purin-9-yl)tetrahydrothiophene-3,4-diol The synthesis was conducted under the same conditions as in the step 3 of the Example 11 by using 3-chlorobenzylamine instead of 3-fluorobenzylamine to obtain the target compound (0.12 g, 85%).

mp 165.0-165.3° C.;

UV (MeOH) $\lambda_{max}$ 274.5 nm;

$^1$H-NMR (DMSO-d$_6$) δ 8.47 (s, 1H), 8.22 (s, 1H), 7.39 (s, 1H), 7.26-7.35 (m, 3H), 5.91 (d, 1H, J=7.2 Hz), 5.53 (d, 1H—OH, J=6.4 Hz), 5.35 (d, 1H—OH, J=4.0 Hz), 4.67-4.71 (m, 2H), 4.33-4.37 (m, 1H), 3.40-3.48 (m, 2H), 2.80 (dd, 1H, J=3.2, 10.4 Hz);

$[α]^{25}_D$-162.5 (c 0.10, DMSO);

FAB-MS m/z 378 [M+H]$^+$.

<Example 13> Preparation of (2R,3R,4S)-2-(6-(3-bromobenzylamino)-9H-purin-9-yl)tetrahydrothiophene-3,4-diol Step 1. Preparation of 6-chloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 11.

Step 2. Preparation of (2R,3S,4S)-2-(6-chloro-9H-purin-9-yl) tetrahydrothiophene-3,4-diol The target compound as a white solid was obtained in the same manner as in the step 2 of the Example 11.

Step 3. Preparation of (2R,3R,4S)-2-(6-(3-bromobenzylamino)-9H-purin-9-yl)tetrahydrothiophene-3,4-diol The synthesis was conducted under the same conditions as in the step 3 of the Example 11 by using 3-bromobenzylamine instead of 3-fluorobenzylamine to obtain the target compound (0.11 g, 70%).

mp 183.0-184.0° C.;

UV (MeOH) $\lambda_{max}$ 270.0 nm;

$^1$H-NMR (DMSO-d$_6$) δ 8.46 (s, 1H), 8.22 (s, 1H), 7.53 (s, 1H), 7.39-7.42 (m, 1H), 7.34-7.35 (m, 1H), 7.24-7.28 (m, 1H), 5.90 (d, 1H, J=7.2 Hz), 5.53 (d, 1H—OH, J=6.4 Hz), 5.35 (d, 1H—OH, J=4.0 Hz), 4.67-4.71 (m, 2H), 4.35-4.37 (m, 1H), 3.41 (dd, 1H, J=4.0, 10.8 Hz), 3.06 (q, 1H, J=7.2 Hz), 2.80 (dd, 1H, J=2.8, 10.8 Hz); $[a_1]^2$D-100.72 (c 0.14, DMSO);

FAB-MS m/z 422 [M+H]$^+$.

<Example 14> Preparation of (2R,3R,4S)-2-(6-(3-iodobenzylamino)-9H-purin-9-yl) tetrahydrothiophene-3,4-diol Step 1. Preparation of 6-chloro-9-((3aR,4R,6aS)-2,2-dimethyltetrahydrothieno[3,4-d][1,3]dioxol-4-yl)-9H-purine The target compound in the form of foam was obtained in the same manner as in the step 1 of the Example 11.

Step 2. Preparation of (2R,3S,4S)-2-(6-chloro-9H-purin-9-yl) tetrahydrothiophene-3,4-diol The target compound as a white solid was obtained in the same manner as in the step 2 of the Example 11.

Step 3. Preparation of (2R,3R,4S)-2-(6-(3-iodobenzylamino)-9H-purin-9-yl)tetrahydrothiophene-3,4-diol The synthesis was conducted under the same conditions as in the step 3 of the Example 11 by using 3-iodobenzylamine instead of 3-fluorobenzylamine to obtain the target compound (0.12 g, 72%).

mp 198.8-199.8° C.;

UV (MeOH) $\lambda_{max}$ 271.5 nm;

$^1$H-NMR (DMSO-d$_6$) δ 8.46 (s, 1H), 8.22 (s, 1H), 7.72 (s, 1H), 7.56-7.59 (m, 1H), 7.35-7.36 (d, 1H, J=7.6 Hz), 7.01-7.12 (m, 1H), 5.90 (d, 1H, J=7.2 Hz), 5.53 (d, 1H—OH, J=6.4 Hz), 5.35 (d, 1H—OH, J=4.4 Hz), 4.67-4.71 (m, 2H), 4.34-4.38 (m, 1H), 3.41 (dd, 1H, J=4.0, 10.8 Hz), 3.16 (d, 1H, J=7.2 Hz), 2.80 (dd, 1H, J=2.8, 10.8 Hz);

$[α]^{25}_D$-97.08 (c 0.14, DMSO);

FAB-MS m/z 470 [M+H]$^+$.

<Example 15> Preparation of (2R,3R,4R)-2-(6-(3-bromobenzylamino)-2-chloro-9H-purin-9-yl)tetrahydrofuran-3,4-diol

Step 1. Preparation of 2,6-dichloro-9-((3aR,4R,6aR)-2,2-dimethyltetrahydrofuro[3,4-d][1,3]dioxol-4-yl)-9H-purine The synthesis was conducted by using (3aR,4R,6aR)-2,2-dimethyltetrahydrofuro[3,4-d][1,3]dioxol-4-ol (702.1 g, 3.472 mmol) obtained in Preparation Example 2 under the same conditions as in the step 1 of the Example 1 to obtain the target compound in the form of oil (793.0 mg, 69%).

UV (MeOH) $\lambda_{max}$ 276.5 nm;
$^1$H-NMR (CDCl$_3$) δ 8.15 (s, 1H), 6.07 (s, 1H), 5.41 (d, 1H, J=6.0 Hz), 5.26-5.29 (m, 1H), 4.25-4.31 (m, 2H), 1.57 (s, 3H), 1.41 (s, 3H);
$[\alpha]^{25}_D$-21.00 (c 0.10, DMSO);
FAB-MS m/z 331 [M+H]$^+$.

Step 2. Preparation of (2R,3R,4R)-2-(2,6-dichloro-9H-purin-9-yl) tetrahydrofuro-3,4-diol The synthesis was conducted by using 2,6-dichloro-9-((3aR,4R,6aS)-2,2-dimethyltetrahydrofuro[3,4-d][1,3]dioxol-4-yl)-9H-purine (900 mg, 2.0 mmol) prepared in the step 1 under the same conditions as in the step 2 to obtain the target compound as a white solid (0.46 g, 80%).

mp 122.7-123.4° C.;
UV (MeOH)?max 276.5 nm;
$^1$H-NMR (DMSO-d$_6$) δ 8.98 (s, 1H), 5.96 (d, 1H, J=6.4 Hz), 5.57 (d, 1H—OH, J=6.0 Hz), 5.32 (d, 1H—OH, J=4.0 Hz), 4.69-4.74 (m, 1H), 4.41 (dd, 1H, J=3.6, 9.2 Hz), 4.29-4.32 (m, 1H), 3.87 (dd, 1H, J=2.0, 9.6 Hz);
$[\alpha]^{25}_D$-68.09 (c 0.14, DMSO);
FAB-MS m/z 291 [M+H]$^+$.

Step 3. Preparation of (2R,3R,4R)-2-(6-(3-bromobenzylamino)-2-chloro-9H-purin-9-yl)tetrahydrofuro-3,4-diol After dissolving (2R,3S,4S)-2-(2,6-dichloro-9H-purin-9-yl)tetrahydrofuro-3,4-diol (1 eq.) prepared in the step 2 and 3-bromobenzylamine (1.5 eq.) in ethanol (5 ml) at room temperature, the reaction mixture was stirred at room temperature for 2-3 h. After completion of the reaction, the reaction mixture was concentrated under reduced pressure, and the residue was subjected to silica gel column chromatography using a dichloromethane:methanol mixed solvent (20:1, v/v) as an eluent to obtain the target compound (0.12 g, 82%).

mp 181.5-181.7° C.;
UV (MeOH) $\lambda_{max}$ 274.5 nm;
$^1$H-NMR (DMSO-d$_6$) δ 8.92 (t, 1H—NH, J=6.0 Hz), 8.43 (S, 1H), 7.55 (s, 1H), 7.44 (d, 1H, J=8.0 Hz), 7.33-7.35 (m, 1H), 7.26-7.30 (m, 1H), 5.81 (d, 1H, J=6.4 Hz), 5.47 (d, 1H, J=6.4 Hz), 5.22 (d, 1H, J=4.0 Hz), 4.66-4.69 (m, 1H), 4.62 (s, 2H), 4.32 (dd, 1H, J=3.6, 9.2 Hz), 4.25 (brs, 1H), 3.80 (dd, 1H, J=1.6, 9.2 Hz);
$[\alpha]^{25}_D$-62.75 (c 0.10, DMSO);
FAB-MS m/z 440 [M+H]$^+$.

<Example 16> Preparation of (2R,3R,4R)-2-(6-(3-iodobenzylamino)-2-chloro-9H-purin-9-yl)tetrahydrofuro-3,4-diol

Step 1. Preparation of 2,6-dichloro-9-((3aR,4R,6aR)-2,2-dimethyltetrahydrofuro[3,4-d][1,3]dioxol-4-yl)-9H-purine The target compound in the form of syrupy foam was obtained in the same manner as in the step 1 of the Example 15.

Step 2. Preparation of (2R,3R,4R)-2-(2,6-dichloro-9H-purin-9-yl) tetrahydrofuro-3,4-diol The target compound as a white solid in the form of a syrup was obtained in the same manner as in the step 2 of the Example 15.

Step 3. Preparation of (2R,3R,4R)-2-(6-(3-iodobenzylamino)-2-chloro-9H-purin-9-yl)tetrahydrofuro-3,4-diol The synthesis was conducted under the same conditions as in the step 3 of the Example 15 by using 3-iodobenzylamine instead of 3-bromobenzylamine to obtain the target compound (0.13 g, 78%).

mp 195.5-195.8° C.;
UV (MeOH) $\lambda_{max}$ 274.0 nm;
$^1$H-NMR (DMSO-d$_6$) δ 8.91 (t, 1H—NH, J=6.4 Hz), 8.44 (s, 1H), 7.75 (s, 1H), 7.61 (d, 1H, J=8.0 Hz), 7.36 (d, 1H, J=7.6 Hz), 7.13 (t, 1H, J=4.0 Hz), 5.81 (d, 1H, J=6.8 Hz), 5.47 (d, 1H—OH, J=6.8 Hz), 5.23 (d, 1H—OH, J=4.0 Hz), 4.72 (dd, 1H, J=6.4, 10.8 Hz), 4.61 (d, 1H, J=6.0 Hz), 4.34 (dd, 1H, J=3.6, 9.2 Hz), 3.81 (dd, 1H, J=1.2, 9.2 Hz);
$[\alpha]^{25}_D$-68.07 (c 0.12, DMSO);
FAB-MS m/z 488 [M+H]$^+$.

<Experimental Example 1> Evaluation of Binding Affinity for Adenosine Receptor The following experiments were performed to evaluate the affinity and selectivity of the derivatives of the present invention to the $A_1$, $A_{2A}$ and $A_3$ receptors in the human adenosine receptor (hAR).

The Chinese hamster ovary (CHO, ATCC; American Cell Line No. CCL-61) cells expressing the adenosine $A_1$ and $A_3$ receptors were cultured in F-12 (Gibco Co., USA) medium supplemented with 10% fetal bovine serum (FBS) and penicillin/streptomycin (100 units/ml and 100 μg/ml) at 37° C. and 5% carbon dioxide. The 50/10/1 buffer solution was placed in a test tube and a predetermined amount of CHO cells expressing a suitable hAR and label ligands (1 nM [$^3$H]CCPA and 0.5 nM [$^{125}$I]AB-MECA) selectively binding to the respective adenosine $A_1$ and $A_3$ receptors were mixed. Various concentrations of the derivatives of the present invention are first dissolved in dimethylsulfoxide (DMSO) and then diluted with buffer solution and the final concentration of DMSO should not exceed 1%, and the cells are incubated in a 37° C. thermostat for 1 hour and the cells were rapidly filtered under reduced pressure using a cell collector (TOMTEC Co., USA). Subsequently, the test tube was washed three times with 3 ml buffer, and radioactivity was determined using a γ-counter. Nonspecific binding was determined in the presence of 10 μM of 5'-N-ethylcarboxamidomadocin (NECA), an unlabeled ligand, under the same conditions as for the determination of total binding, and the equilibrium constant $K_i$ was determined according to the Cheng-Prusoff equation with the assumption that the $K_d$ value of [$^{125}$I]AB-MECA was 1.48 nM. Specific binding was calculated by subtracting non-specific binding from total binding. From the measured specific binding, the bonding affinity of each sample of the various receptors was determined.

In addition, the bonding of $A_{2A}$ receptor expressed in HEK 293 cells (human kidney endothelial cell line) and the [$^3$H]CGS-21680 (2-((4-(2-carboxyethyl)phenyl)ethylamino)-5'-N-ethylcarbamoyl)adenosine) which is label ligand, is measured as follows: Adenosine deaminase is added to the cerebral meninges at 30° C. for 30 minutes and during the incubation with radioactive ligand and the $IC_{50}$ values for the compounds of the individual examples were determined at 6 and more different concentrations, and the $K_i$ values were determined by a plotting program using this value.

Table 1 shows the $K_i$ values obtained from the results of the substituent and binding affinity of the compounds of the examples according to the present invention.

the human adenosine $A_3$ receptor, the example compounds in which the 3-position of the benzene ring is substituted are more preferred over the 2- or 4-substituted compounds or the 2,5-disubstituted compounds. Also, the compounds of Examples 15 and 16, which are adenosine derivatives having an oxonucleoside form of 4'-O, also showed high binding affinity and selectivity, but were not better than adenosine derivatives having the corresponding 4'-S thionucleoside form and the compounds of Examples 3 and 4, and the compounds of Examples 10 to 14 in which the chloro group at the 2-position of the purine base was substituted with hydrogen were more excellent in affinity and selectivity than the 2-chloro compounds.

<Experimental Example 2> Antagonistic Effect and cAMP Inhibition Test on Adenosine $A_3$ Receptor Using Derivatives of Present Invention In order to investigate whether the derivatives of the present invention have an effect as antagonists against the human adenosine $A_3$ receptor, CHO cells were treated with the compound of Example 4 and CI-IB-MECA to perform antagonistic effects and cAMP inhibition experiments of the derivatives of the present invention.

TABLE 1

| | substituents | | | K(nM) or % | | |
|---|---|---|---|---|---|---|
| Example | A | R | Y | $hA_1$ | $hA_{2A}$ | $hA_3$ |
| 1 | S | 3-fluorobenzyl | Cl | 19.8% | 47.6% | 7.4 ± 1.3 |
| 2 | S | 3-chlorobenzyl | Cl | 37.9% | 17.7% | 1.66 ± 0.90 |
| 3 | S | 3-bromobenzyl | Cl | 34.2% | 18.4% | 8.99 ± 5.17 |
| 4 | S | 3-iodobenzyl | Cl | 2490 ± 940 | 341 ± 75 | 4.16 ± 0.50 |
| 5 | S | 2-chlorobenzyl | Cl | 12.8% | 1600 ± 135 | 25.8 ± 6.3 |
| 6 | S | 5-chloro-2-methoxybenzyl | Cl | 23.8% | 4020 ± 1750 | 12.7 ± 3.7 |
| 7 | S | 2-methoxybenzyl | Cl | 9.4% | 17.5% | 19.9 ± 7.1 |
| 8 | S | 1-naphtyl | Cl | 22.0% | −8.3% | 24.8 ± 8.1 |
| 9 | S | 3-toluic acid | Cl | 13.1% | −0.18% | 41.5% |
| 10 | S | methyl | Cl | 55.4 ± 1.8% | 45.0 ± 1.4% | 3.69 ± 0.25 |
| 11 | S | 3-fluorobenzyl | H | 1430 ± 420 | 1260 ± 330 | 7.3 ± 0.6 |
| 12 | S | 3-chlorobenzyl | H | 860 ± 210 | 440 ± 110 | 1.5 ± 0.4 |
| 13 | S | 3-bromobenzyl | H | 790 ± 190 | 420 ± 32 | 6.8 ± 3.4 |
| 14 | S | 3-iodobenzyl | H | 530 ± 97 | 230 ± 65 | 2.5 ± 1.0 |
| 15 | O | 3-bromobenzyl | Cl | 39.8% | 22.8% | 13.0 ± 6.9 |
| 16 | O | 3-iodobenzyl | Cl | 37.7% | 28.6% | 42.9 ± 8.9 |

As shown in Table 1, the compounds of the present invention exhibited high binding affinity for the human adenosine $A_3$ receptor and low affinity for the adenosine $A_1$ and $A_{2A}$ receptors, i.e., high selectivity. In particular, the compound of Example 12 of the present invention exhibited the highest affinity for the $hA_3$ receptor with affinity constant $K_i$ value of 1.50±0.40 nM and then the binding affinity is high in order of the compound of Example 2 ($K_i$=1.66±0.90 nM), the compound of Example 14 ($K_i$=2.50±1.00 nM), the compound of Example 10 ($K_i$=3.69±0.25 nM) and the compound of Example 4 ($K_i$=4.16±0.50 nM). The compound of Example 4 of the present invention also showed a high affinity ($K_i$=3.89±1.15 nM) for adenosine $A_3$ receptor in rats expressed in Chinese hamster ovary (CHO) cells and the human adenosine $A_{2B}$ receptor did not show activity as an agonist or an antagonist.

In addition, the binding affinities in the example compounds having a halobenzyl substituent show in the order Cl>I>F>Br, the compound of Example 2 having 3-chlorobenzyl has higher affinity for $hA_3$ adenosine receptor than the compound of Example 5 having 2-chlorobenzyl ($K_i$=25.8±6.3 nM). In addition, as for the binding affinity of As shown in FIG. 1, for the human adenosine $A_3$ receptor, the effect of an agonist of CI-IB-MECA as a 100% pure agonist in CHO cells treated with the compound of Example 4 at different concentrations was confirmed to be inhibited depending on the concentration of the compound of Example 4. This is a result indicating that the compound of the present invention and CI-IB-MECA competitively act on the same binding site of the receptor. In addition, from a result of cAMP inhibition experiments mediated by the human adenosine $A_3$ receptor in CHO cells, it can be seen that the compounds of the present invention are 100% pure adenosine $A_3$ antagonists. Therefore, the compounds synthesized in the present invention had a dissociation constants KB measured by Schild analysis of 1.92 nM.

<Experimental Examples 3 to 6> Measurement of Anti-Inflammatory Activity of Derivatives of Present Invention In order to investigate the anti-inflammatory activity of the derivatives of the present invention, the animal experiments were performed as below. Seven-week-old male ICR mice were treated with TPA (12-O-tetradecanoylphorbol 13-acetate, 20 l) in the right ear. The compounds of Examples 1 to 16 of the present invention were diluted to a concentration of 0.5% in acetone (20 l) or distilled water or a mixed solvent of DMSO and acetone (its composition is shown in Tables 2 to 5) and was administered to a mouse in 15 minutes. The same experiment was performed by treating hydrocortisone used as a treatment agent for inflammation as a control at the same concentration.

Subsequently, secondly, the adenosine derivative compound of the present invention was treated after 6 hours from TPA treatment. Twenty-four hours after TPA treatment, the animals were euthanized using the cervical dislocation method. Then, a right ear sample was obtained using a 6 mm diameter punch. The activity could be confirmed by weighing using a microbalance. The inhibition rate (%) was calculated using the following Equation 1. The treatment compositions and treatment amounts of Experimental Examples 3 to 6 are shown in Tables 2 to 5, and the results of measuring the anti-inflammatory activity are shown in FIG. 2 to FIG. 5.

$$\text{Inhibition rate (\%)} = 1 - \frac{(\text{weight of sample treated with Example compound} - \text{weight of untreated sample})}{\text{weight of sample treated with TPA only} - \text{weight of untreated sample weight}} \quad [\text{Equation 1}]$$

TABLE 2

| Experimental Example 3 | Treatment composition | Treatment amount |
|---|---|---|
| 3-1 | No treatment | — |
| 3-2 | TPA only | 20 μl |
| 3-3 | TPA + acetone treatment | 20 μl + 20 μl |
| 3-4 | TPA + acetone + compound of Example 2 | 20 μl + 0.5%/20 μl |
| 3-5 | TPA + acetone + compound of Example 3 | 20 μl + 0.5%/20 μl |
| 3-6 | TPA + acetone + compound of Example 4 | 20 μl + 0.5%/20 μl |
| 3-7 | TPA + acetone + hydrocortisone | 20 μl + 0.5%/20 μl |

TABLE 3

| Experimental Example 4 | Treatment composition | Treatment amount |
|---|---|---|
| 4-1 | No treatment | — |
| 4-2 | TPA only | 20 μl |
| 4-3 | TPA + acetone treatment | 20 μl + 20 μl |
| 4-4 | TPA + acetone + compound of Example 1 | 20 μl + 0.5%/20 μl |
| 4-5 | TPA + acetone + compound of Example 6 | 20 μl + 0.5%/20 μl |
| 4-6 | TPA + acetone + hydrocortisone | 20 μl + 0.5%/20 μl |

TABLE 4

| Experimental Example 5 | Treatment composition | Treatment amount |
|---|---|---|
| 5-1 | No treatment | — |
| 5-2 | TPA only | 20 μl |
| 5-3 | TPA + mixed solvent treatment (mixed solvent = DI water:acetone = 1:4) | 20 μl + 20 μl |
| 5-4 | TPA + mixed solvent + compound of Example 5 | 20 μl + 0.5%/20 μl |
| 5-5 | TPA + mixed solvent + compound of Example 7 | 20 μl + 0.5%/20 μl |
| 5-6 | TPA + mixed solvent + compound of Example 8 | 20 μl + 0.5%/20 μl |
| 5-7 | TPA + mixed solvent + hydrocortisone | 20 μl + 0.5%/20 μl |

TABLE 5

| Experimental Example 6 | Treatment composition | Treatment amount |
|---|---|---|
| 6-1 | No treatment | — |
| 6-2 | TPA only | 20 μl |
| 6-3 | TPA + mixed solvent treatment (mixed solvent = DMSO:acetone = 1:9) | 20 μl + 20 μl |
| 6-4 | TPA + mixed solvent + compound of Example 15 | 20 μl + 0.5%/20 μl |
| 6-5 | TPA + mixed solvent + compound of Example 16 | 20 μl + 0.5%/20 μl |
| 6-6 | TPA + mixed solvent + hydrocortisone | 20 μl + 0.5%/20 μl |

As shown in FIG. 2, after diluting the compounds of Examples 2, 3 and 4 in acetone, mice were treated with them to measure the anti-inflammatory activity. The TPA-induced mouse ear edema was reduced by a small amount, although it is very little change compared to hydrocortisone used as a control.

Figure 3:
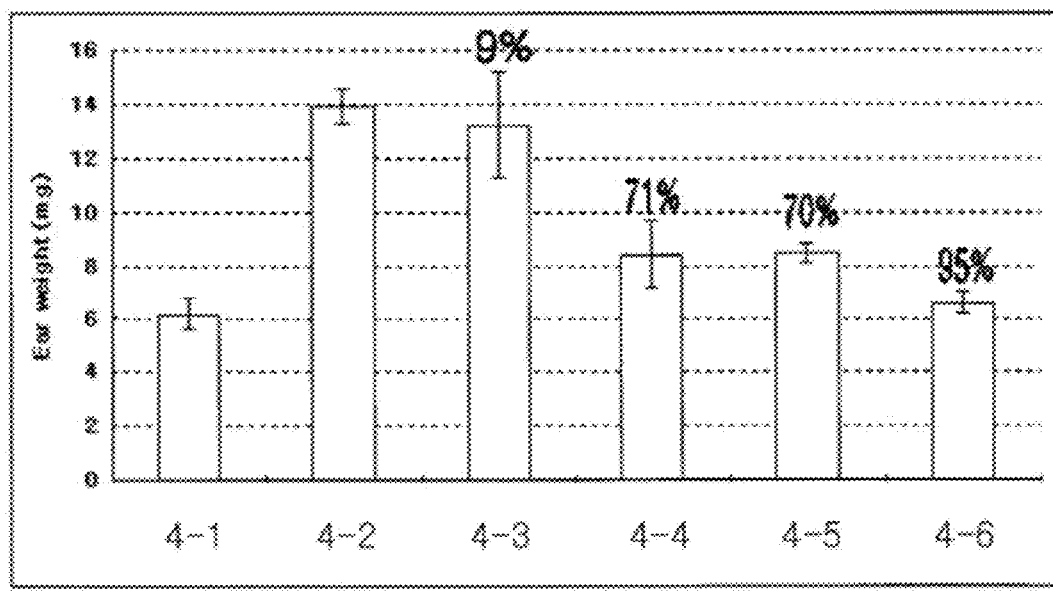
FIG. 3 shows the anti-inflammatory activity of the compounds of the present invention (Examples 1 and 6) by the animal experiments.

As shown in FIG. 3, after diluting the compounds of Examples 1 and 6 in acetone, mice were treated with them to measure the anti-inflammatory activity and It was found that the inhibition rate was significantly increased at least four times as compared with the compounds of Examples 2 to 4 of FIG. 2.

As shown in FIG. 4, the anti-inflammatory activities of the compounds of Examples 5, 6 and 7 of the present invention diluted to 0.5% in a mixed solvent of distilled water and acetone (1:4) were 17% and 34% and 53% of inflammation inhibition rate, respectively.

Figure 5:
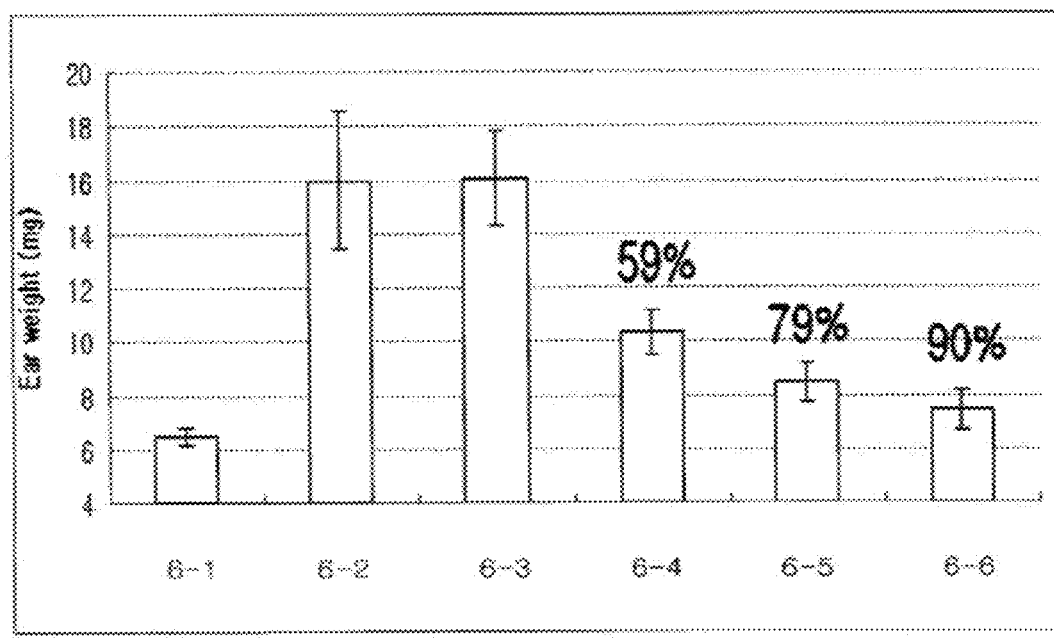
FIG. 5 shows the anti-inflammatory activity of the compounds of the present invention (Examples 15 and 16) by the animal experiments.

As shown in FIG. 5, the inflammation inhibition rates by the compounds of Examples 15 and 16 diluted to 0.5% in a mixed solvent of DMSO and acetone (1:9) were 59% and 79%, respectively, which indicated that the compound had anti-inflammatory activity.

<Experimental Example 7> Toxicity Test

In order to test the toxicity of the example compounds of the present invention, animal experiments were performed. Three each mice of 25 J 5 g ICR mice (central laboratory animals) and 235±10 g Specific Pathogen Free (SPF) Sprague Dawley (central laboratory animals) rats were divided into three groups and the compound of Example 2 was intraperitoneally administered at doses of 20 mg/kg, 10 mg/kg and 1 mg/kg, respectively, and then observed for toxicity for 24 hours.

As a result of the experiment, no deaths were observed in all of the three groups, and there was no apparent symptom with the control group including weight gain, feed consumption, and the like, and thus it was confirmed that the derivative compound of the present invention is a safe drug.

<Experimental Example 8> Test for Effect of Eye-Drop Formulation Comprising Derivatives of Present Invention on Intraocular Pressure Reduction (1)

The following animal experiments were performed to examine the intraocular pressure decrease effect according to eye drop administration of the derivatives of the present invention. The compound of Example 2 was mixed with a buffer solution of pH 6.8 in which Cremophor EL, glycerin, citric acid and methylparaben were dissolved to prepare eye drops containing the compounds of Example 2 at 250 µM, 500 µM and 750 µM, respectively and were administered by eye drop to 2.5-3.0 kg of normal male New Zealand white rabbit by 2 drops, respectively. As a positive control, Xalatan®, an eye drop for treating glaucoma, and as a negative control, no treatment was given to the experimental animals.

Figure 6:
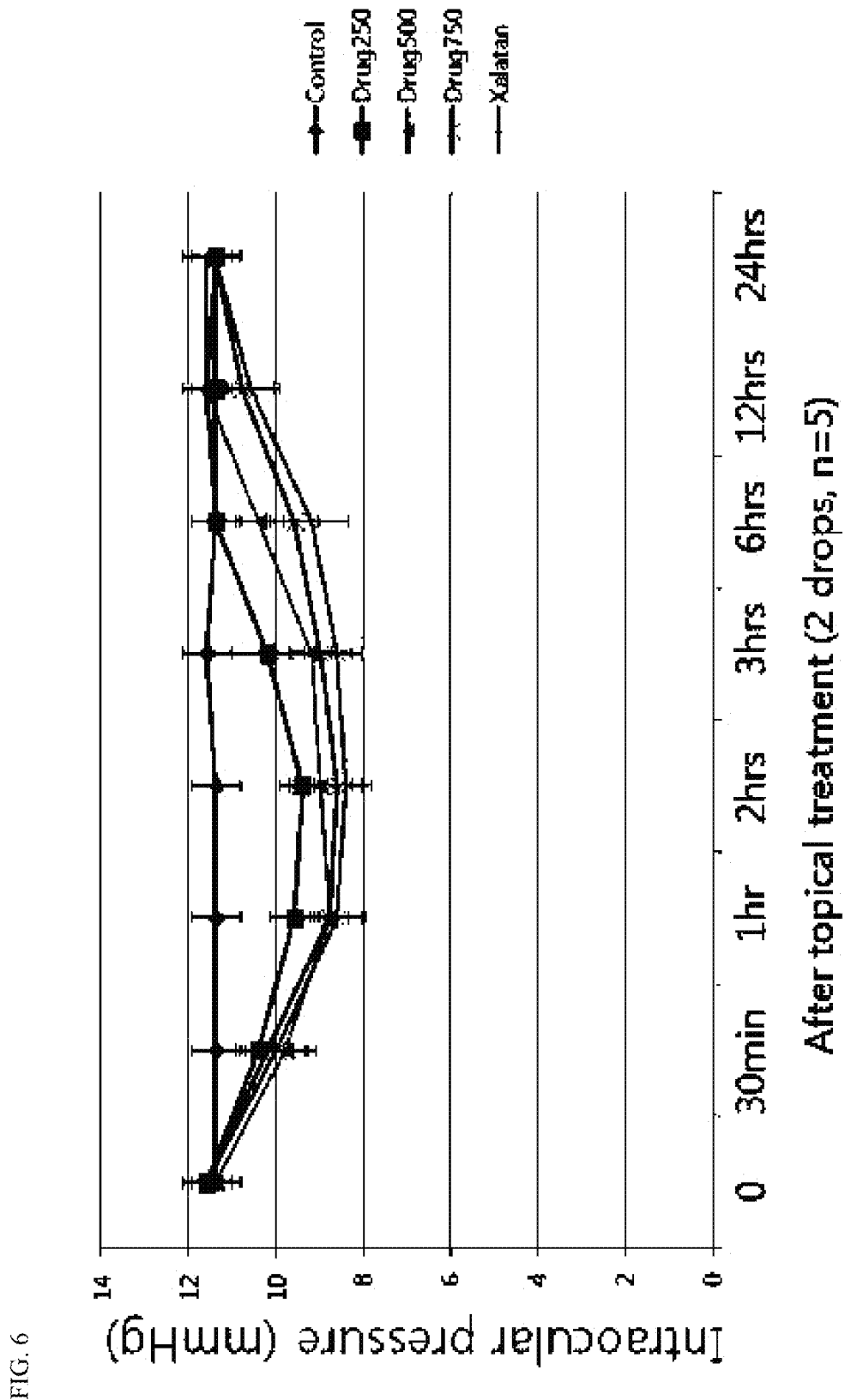
FIG. 6 shows the results of measuring the intraocular pressure of a laboratory animal in Experimental Example 8.

Then, the intraocular pressure of the laboratory animals was measured after 30 minutes, 1 hour, 2 hours, 3 hours, 6 hours, 12 hours and 24 hours, and the results are shown in FIG. 6. In FIG. 6, Control represents a negative control, Drug 250, 500 and 750 are eye drops containing the compound of Example 2 at 250 µM, 500 µM and 750 µM, respectively, and Xalatan is a positive control.

As shown in FIG. 6, it can be confirmed that the rabbit administered with the eye drops comprising the adenosine derivative of the present invention had an effect of reducing the intraocular pressure depending on the dose of the eye drops.

<Experimental Example 9> Test for Effect of Eye-Drop Formulation Comprising Derivatives of Present Invention on Intraocular Pressure Reduction (2)

The following animal experiments were performed to examine the intraocular pressure decrease effect according to eye drop administration of the derivatives of the present invention. The eye drops prepared in Experimental Example 8 were administered to the DAB 2J mice induced glaucoma twice daily. As a positive control group, Xalatan®, an eye drop used as a glaucoma treatment agent, was administered in the same manner, and no treatment was given to the laboratory animals as a negative control group.

Figure 7:
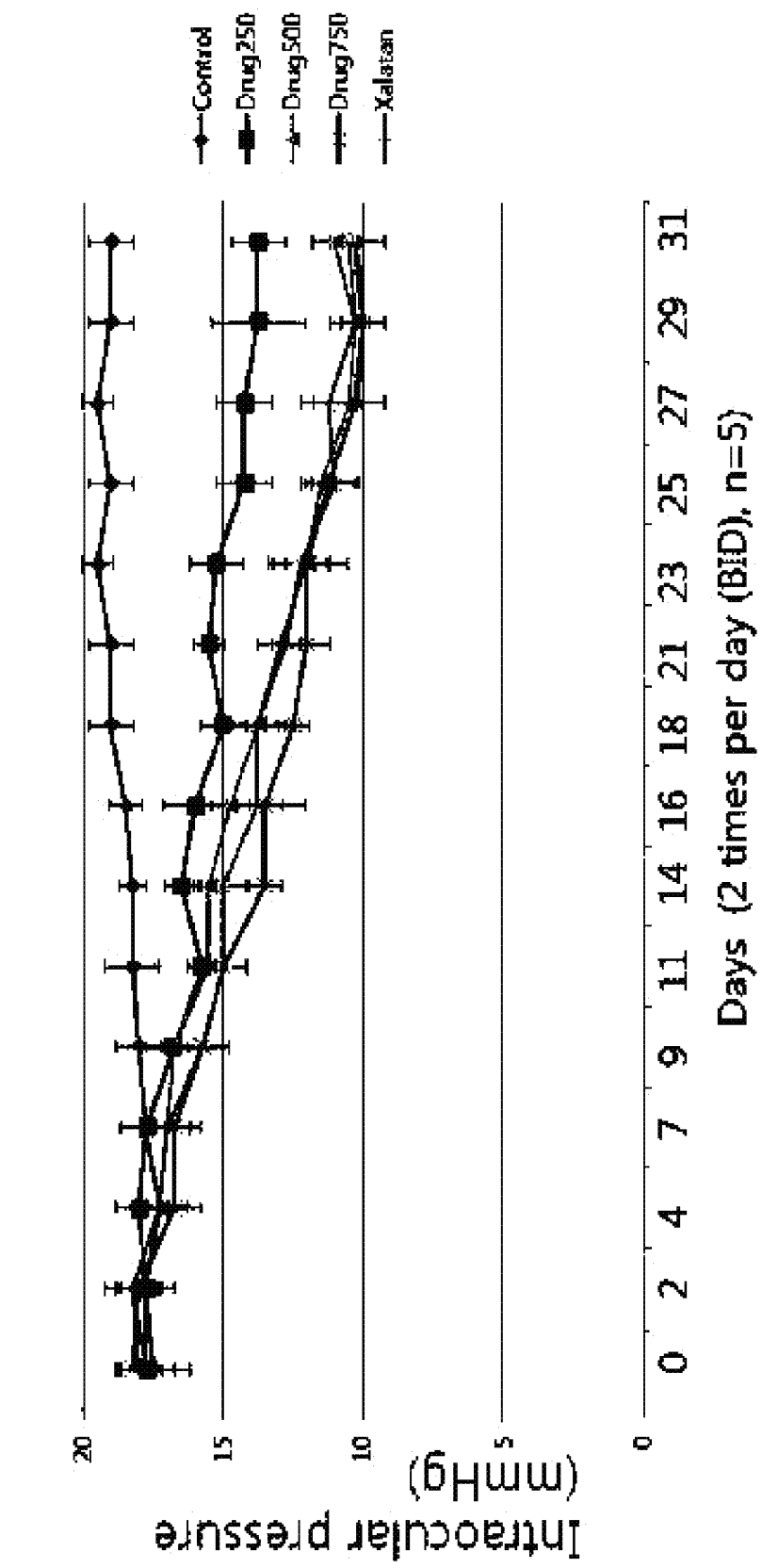
FIG. 7 shows the results of measuring the intraocular pressure of a laboratory animal in Experimental Example 9.
Figure 8:
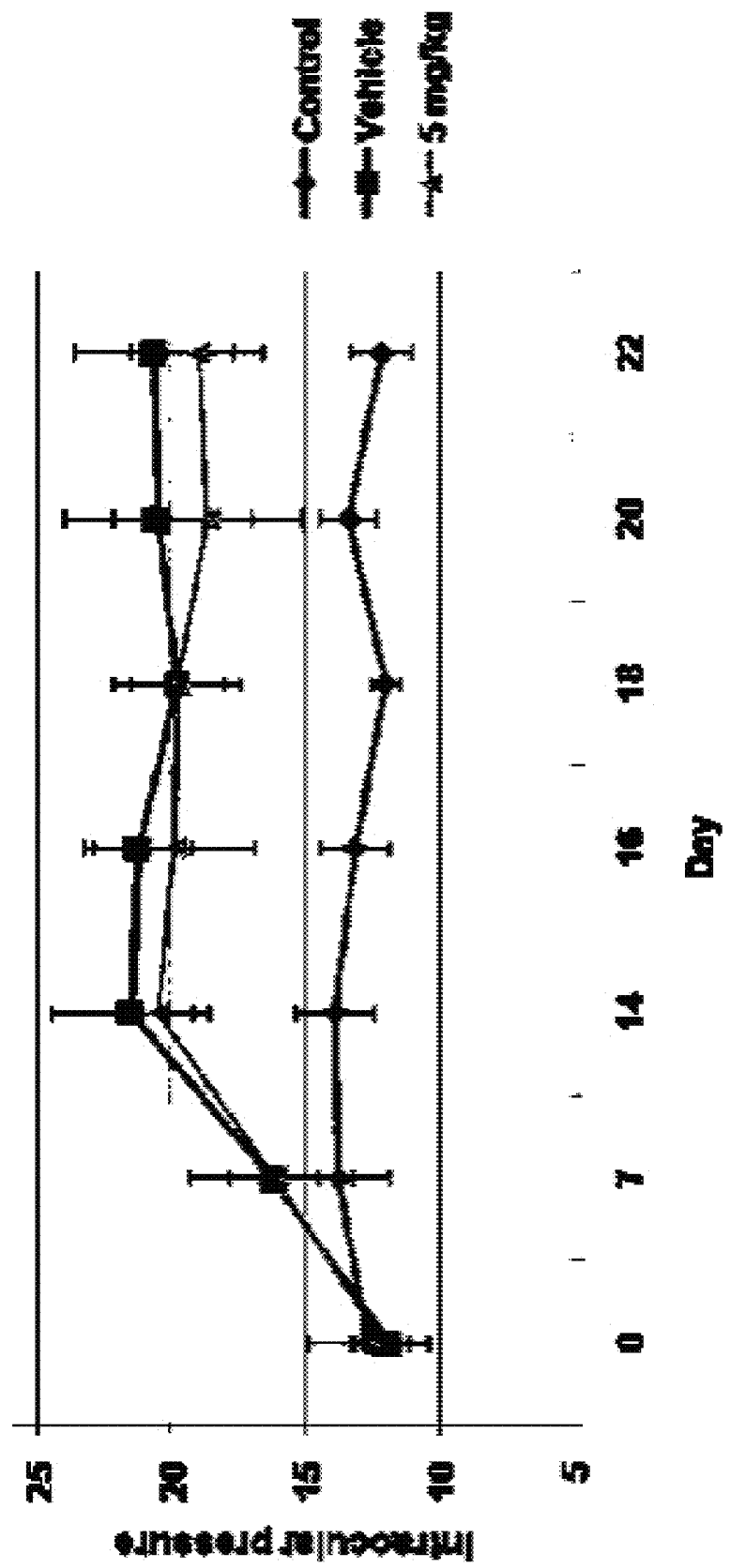
FIG. 8 to FIG. 12 are graphs showing the results of measuring the intraocular pressure of laboratory animals in Experimental Example 10.
Figure 9:
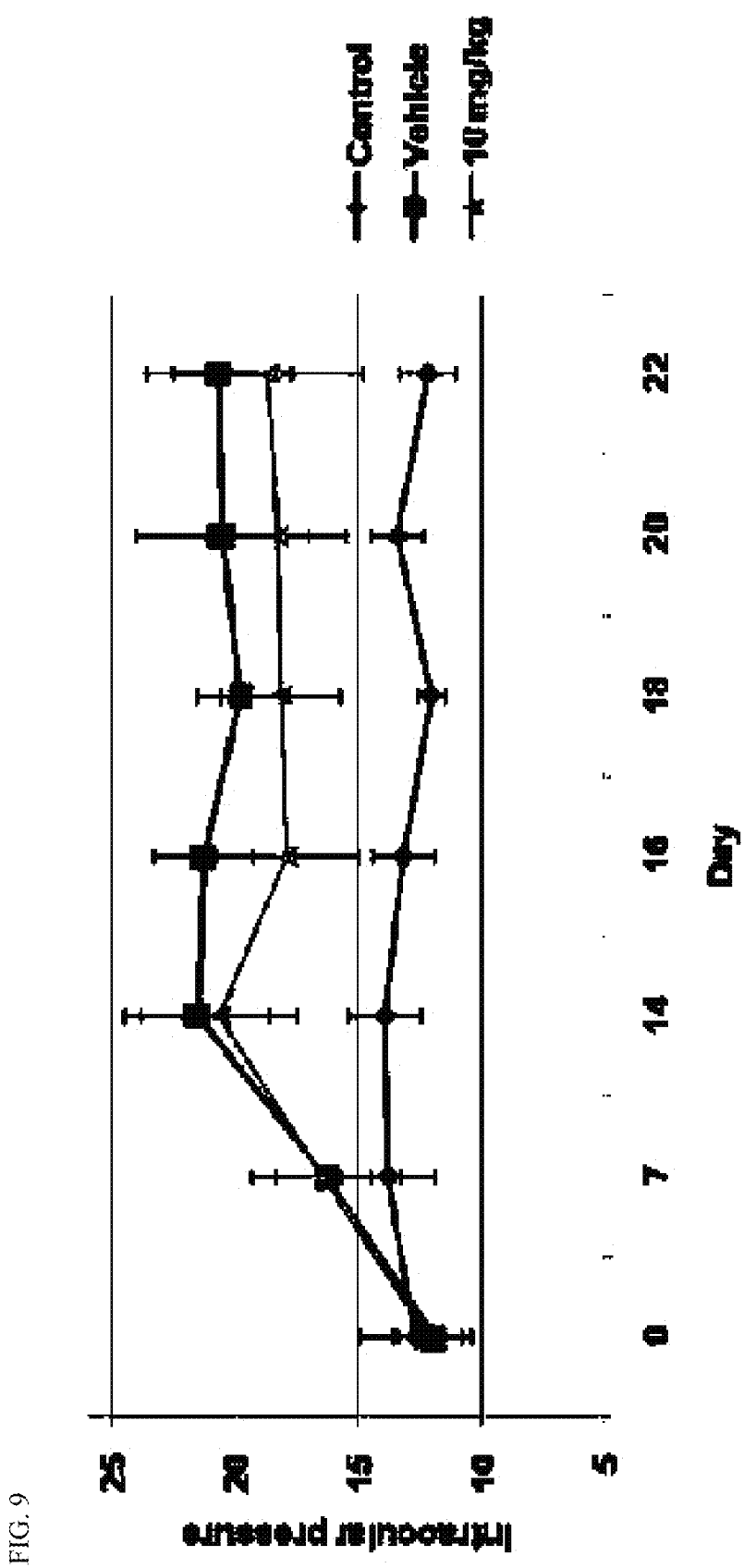
Figure 10:
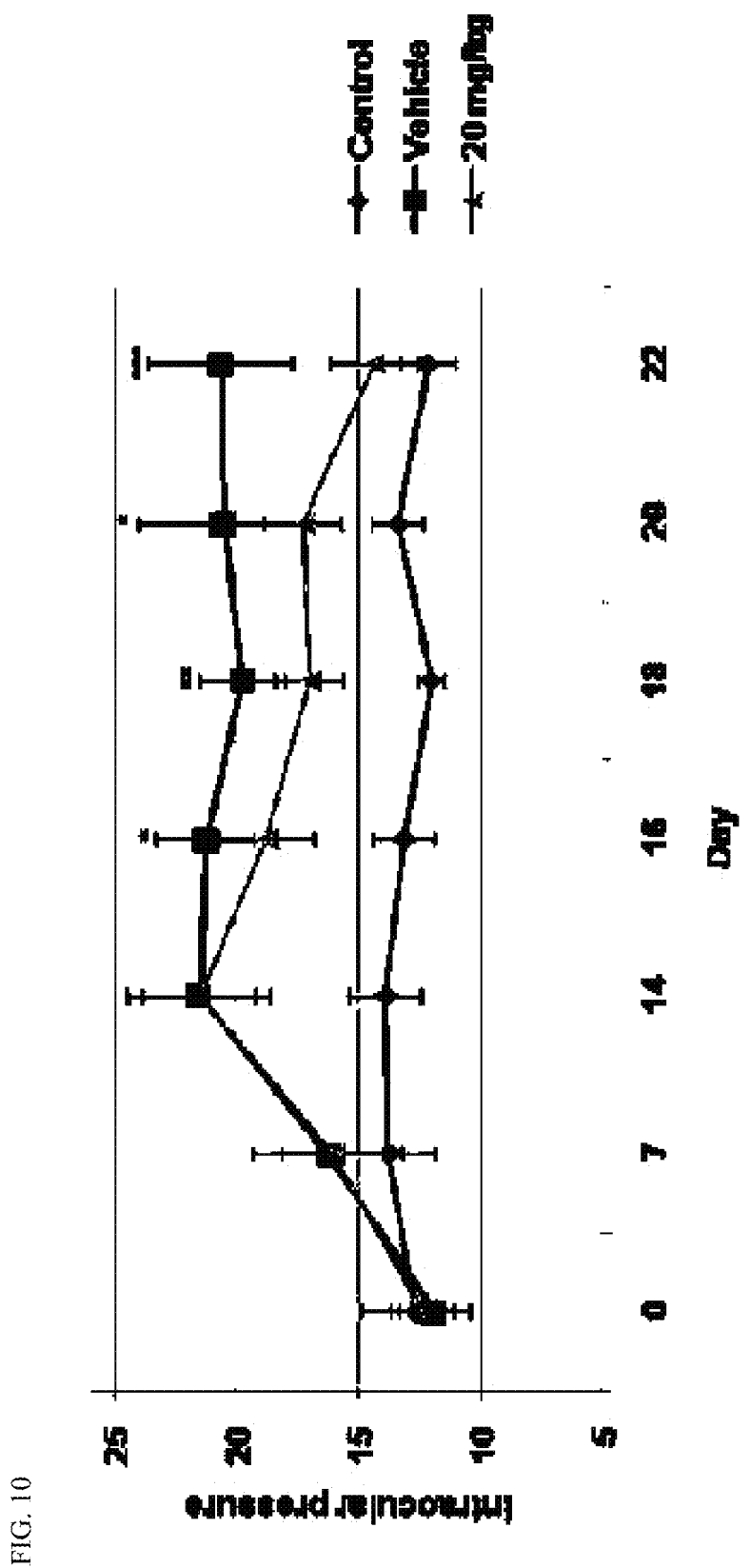
Figure 11:
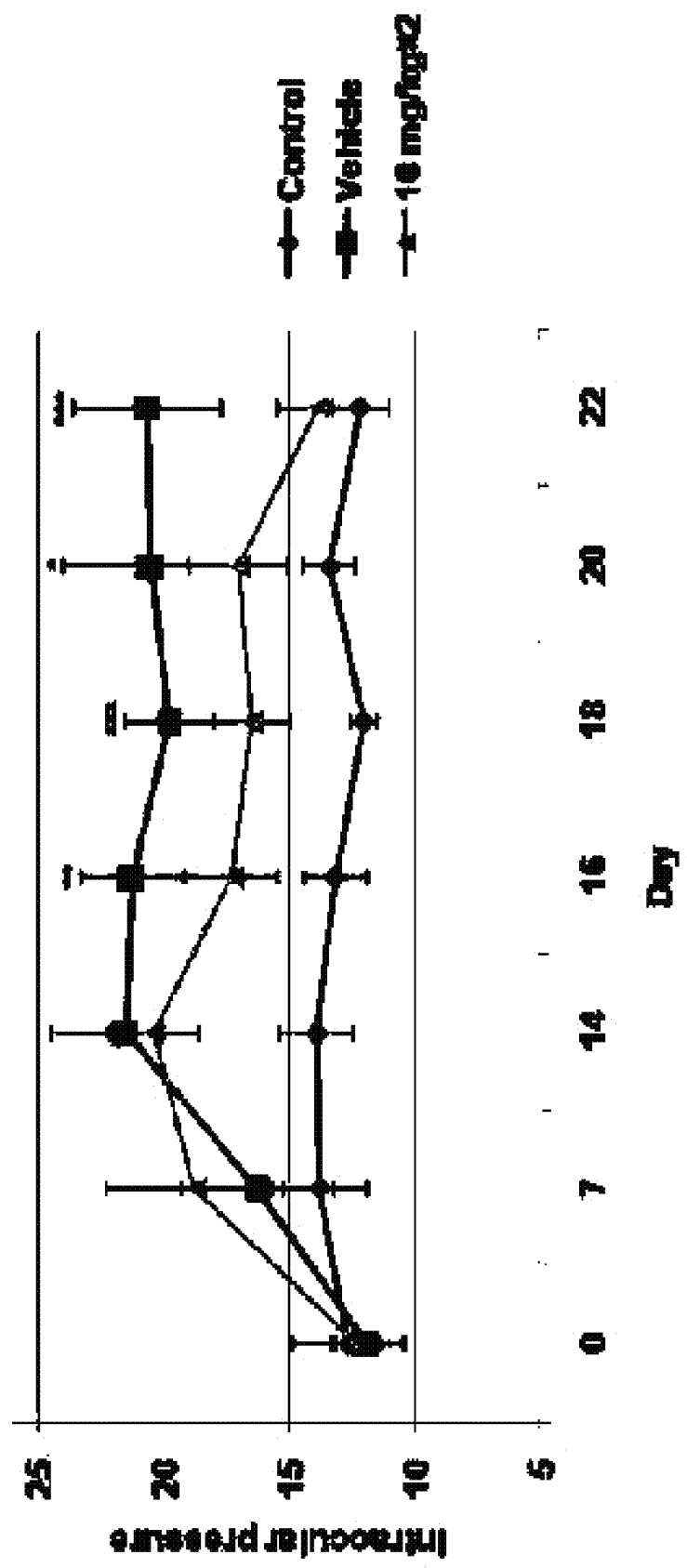
Figure 12:
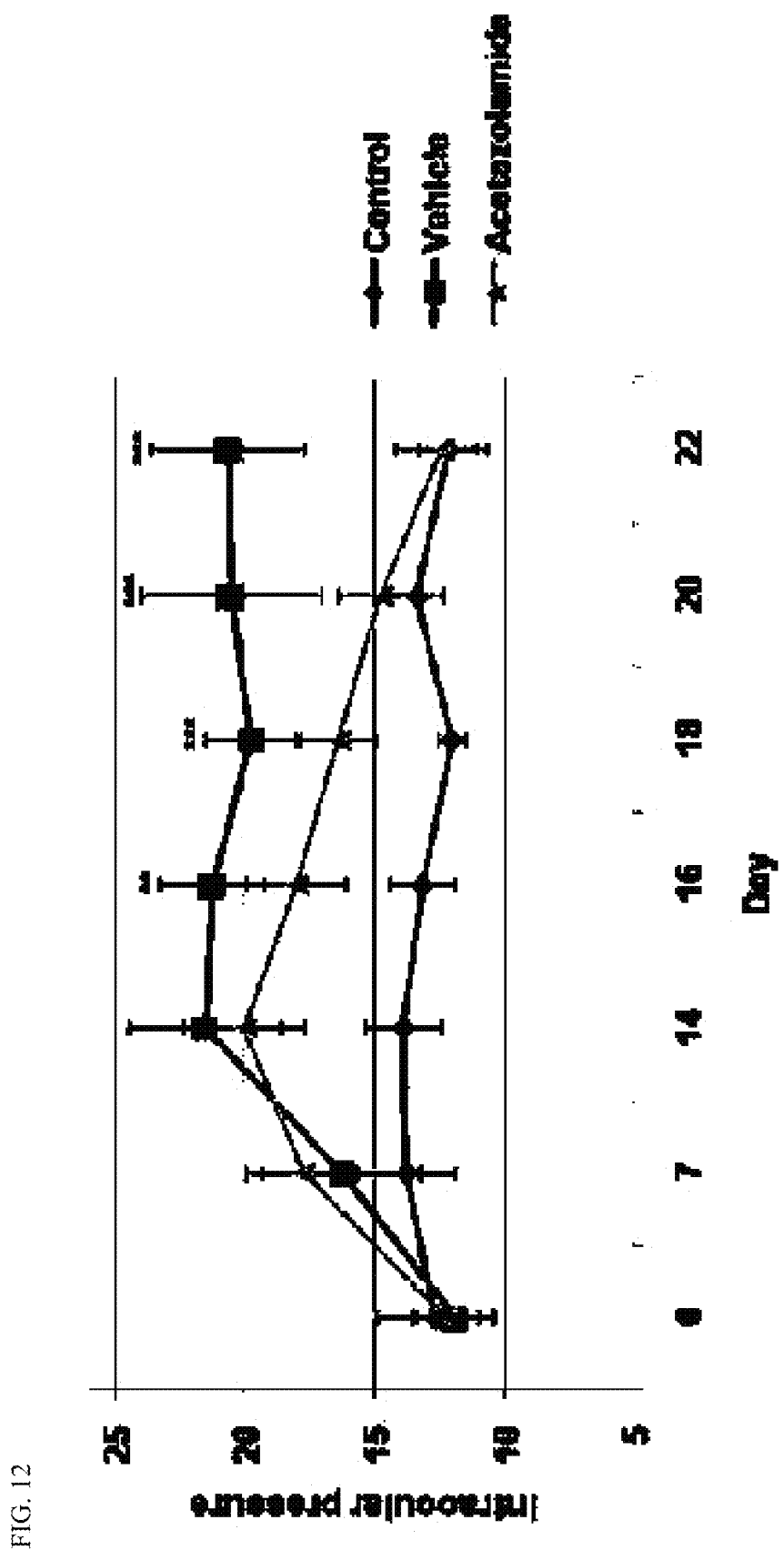

Then, the intraocular pressure of the laboratory animals was measured every 2 days during the period of administration of the eye drops, and the results are shown in FIG. 7. In FIG. 7, Control represents a negative control, Drug 250, 500 and 750 represent eye drops comprising the compound of Example 2 at 250 µM, 500 µM and 750 µM, respectively, and Xalatan is a positive control.

As shown in FIG. 7, it can be confirmed that the mouse administered with the eye drops comprising the adenosine derivative of the present invention had an effect of reducing the intraocular pressure depending on the dose of the eye drops.

<Experimental Example 10> Intraocular Pressure Reduction Test Following the Oral Administration of Derivatives of Present Invention In order to examine the intraocular pressure lowering effect of the derivatives of the present invention, the following animal experiments were performed. Dexamethasone was administered by eye drop to 10-week-old normal C57BL/6J mice to increase intraocular pressure and the compound of Example 2 by 5 mg/kg of once a day, 10 mg/kg once a day, 20 mg/kg once a day, and 10 mg/kg twice a day were orally administered together with the excipients DMSO, PEG400 and saline to each mouse. As controls, only the above excipients were administered to laboratory animals with elevated intraocular pressure once a day, or experimental animals were not treated with dexamethasone or with 4.17 mg/kg of acetazolamide, an intraocular pressure lowering agent, once a day.

Then, the intraocular pressure of the test animal was measured at predetermined intervals for 22 days, and the results are shown in FIG. 8 to FIG. 12. In FIG. 8 to FIG. 12, Control represents a control group in which dexamethasone is not treated to laboratory animals, Vehicle represents a control group in which only excipients were orally administered to laboratory animals with elevated intraocular pressure, and Acetazolamide represents control group in which acetazolamide, an intraocular pressure lowering agent was orally administered to laboratory animals with elevated intraocular pressure.

As shown in FIG. 8 to FIG. 12, mice administered orally with the adenosine derivative of the present invention showed a reduction in intraocular pressure, which was dependent on the dose of the adenosine derivative. Mice in which the compound of Example 2 was administered at a dose of 20 mg/kg once a day and 10 mg/kg twice a day showed similar intraocular pressure to that of the normal mice control group without treatment with dexamethasone from the 22nd day after administration.

<Experimental Example 11> Anti-Fibrotic Effect of Adenosine Derivatives of Present Invention on Trabecular Meshwork Tissue In order to investigate whether the derivatives of the present invention have an effect of inhibiting fibrosis of the trabecular meshwork tissue of the eye, the following animal experiments were performed.

Figure 13:
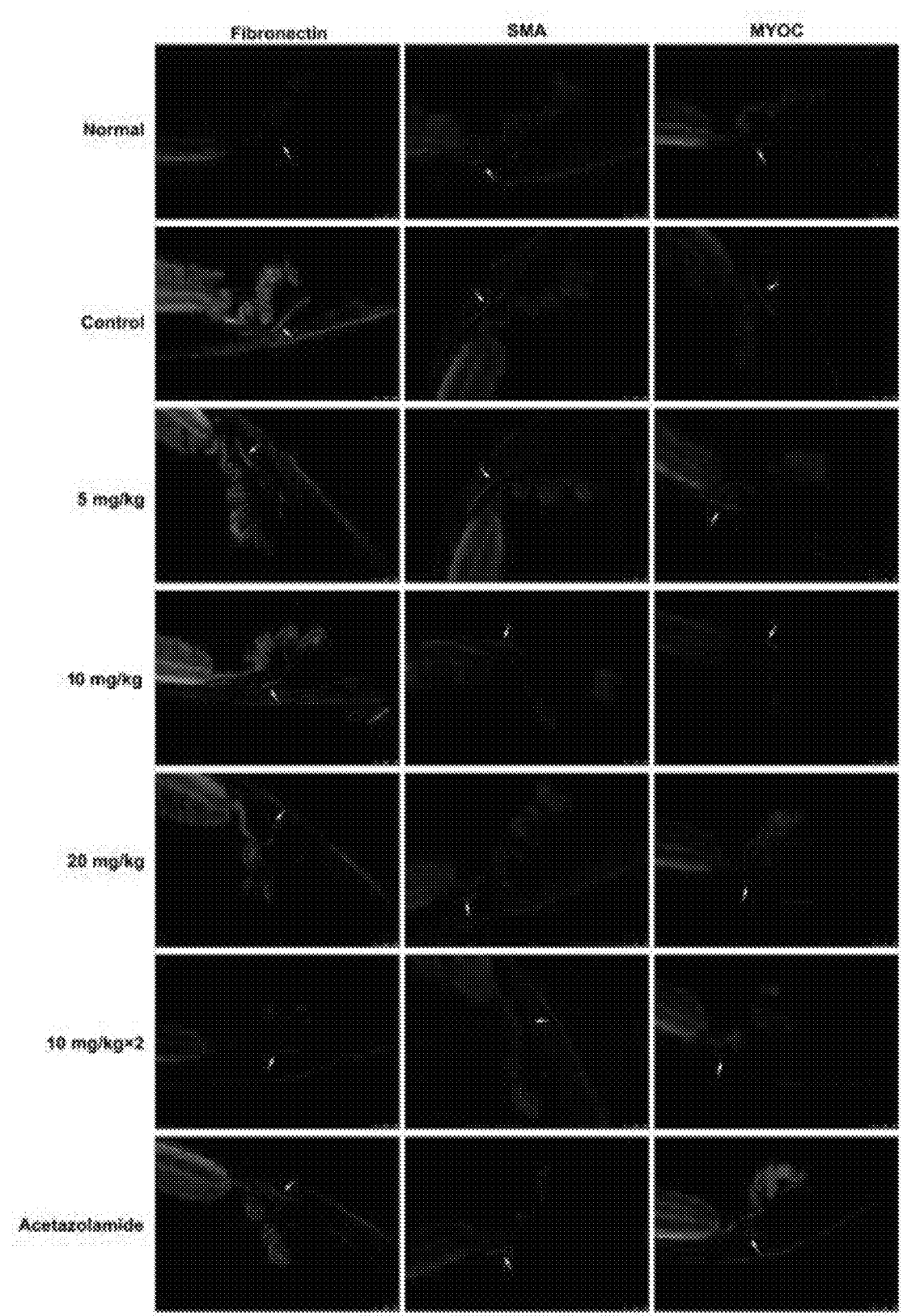
FIG. 13 is a photograph showing changes in the expression of extracellular matrix proteins (Fibronectin, SMA and MYOC) in the trabecular meshwork tissue of laboratory animal eye in Experimental Example 11.

In Experimental Example 10, the ocular tissues of each laboratory animal after measurement of intraocular pressure were extracted and sectioned and immunostaining using antibody was performed to confirm the expression of extracellular matrix proteins (Fibronectin, SMA and MYOC) and the results are shown in FIG. 13. In FIG. 13, Normal represents the trabecular meshwork of the animal which dexamethasone was not treated with in Experimental Example 10, Control represents the trabecular meshwork tissue of the animal to which only the excipient was administered in Experimental Example 10, Acetazolamide represents the trabecular meshwork tissue of the animal to which acetazolamide was administered in Experimental Example 10. Fluorescently stained tissue was observed under fluorescence microscope under the same conditions (magnification 200×, exposure time 1 sec).

As shown in FIG. 13, in the trabecular meshwork tissue of the animal to which only excipients were administered or acetazolamide, an intraocular pressure lowering agent was administered, increased expression of fibronectin, smooth muscle actin (SMA) and myocilin (MYOC) protein was observed and while the expression of the three proteins was confirmed to be greatly reduced in the trabecular meshwork tissue of the animal to which the compound of Example 2 was administered at a dose of 20 mg/kg once a day and at a dose of 10 mg/kg twice a day.

<Experimental Example 12> Test for Effect of Adenosine Derivative of Present Invention on MMP Enzyme and TIMP Enzyme Protein Expression In order to confirm whether the anti-fibrotic effect of the adenosine derivative of the present invention on the trabecular meshwork tissue is related to the expression of MMP and TIMP enzyme protein which regulate the extracellular matrix changes, the following animal experiments were performed.

Figure 14:
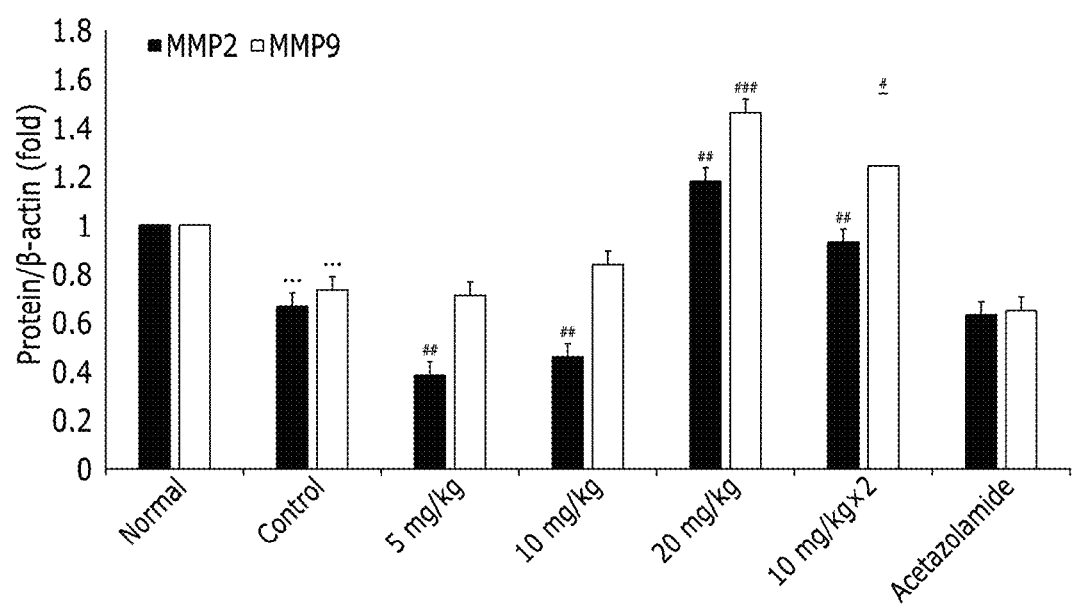
FIG. 14 to FIG. 17 are graphs showing the measurement results of MMP and TIMP enzyme proteins and mRNA expression levels in the trabecular meshwork tissue of laboratory animal eye in Experimental Example 12.
Figure 15:
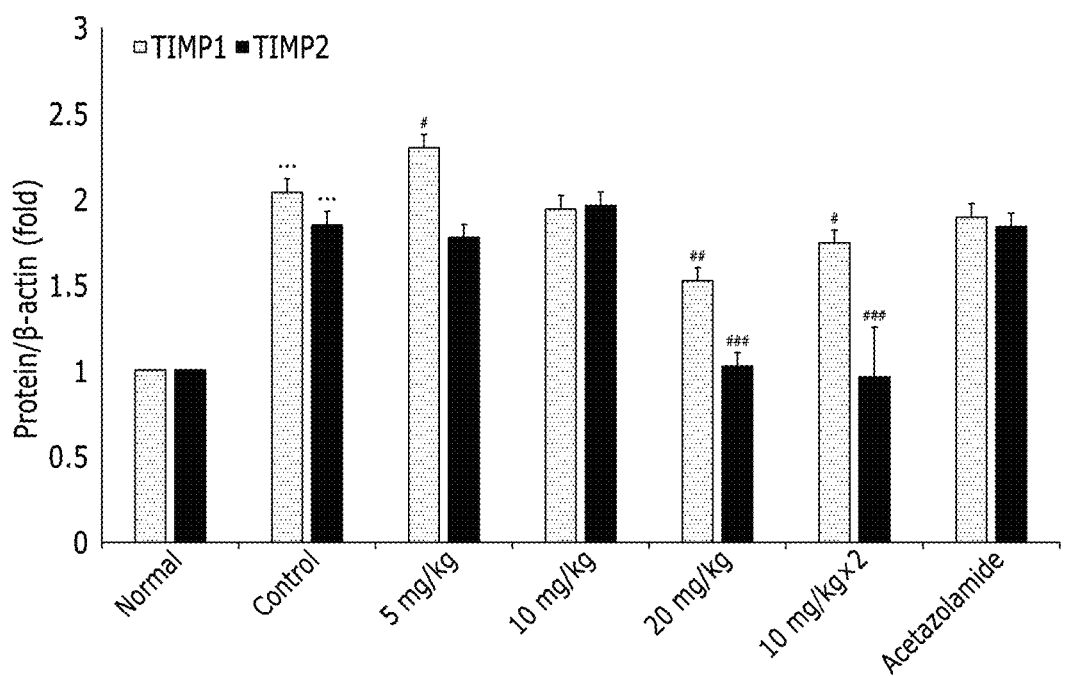
Figure 16:
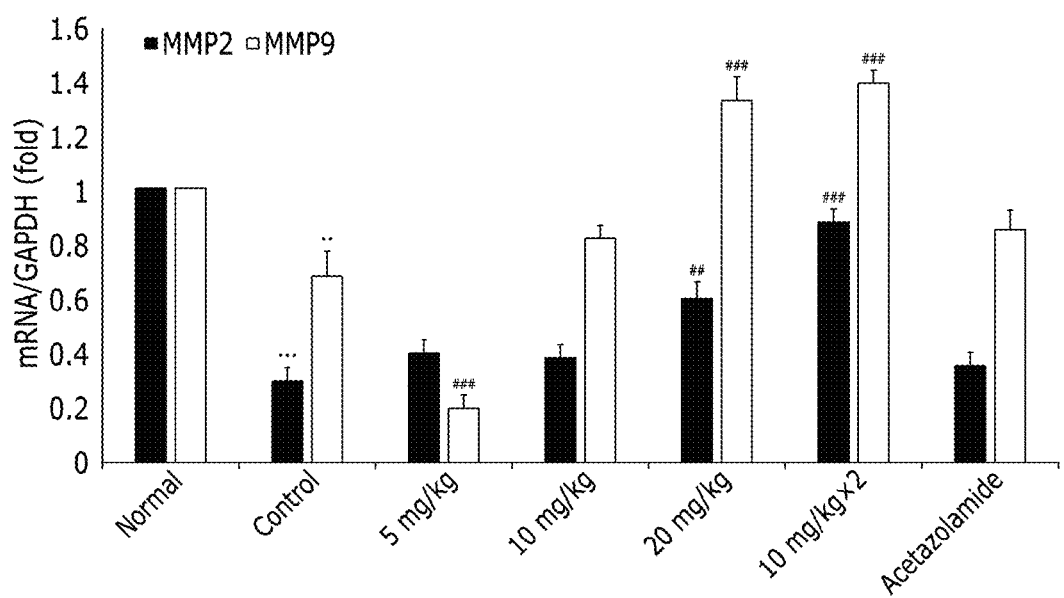
Figure 17:
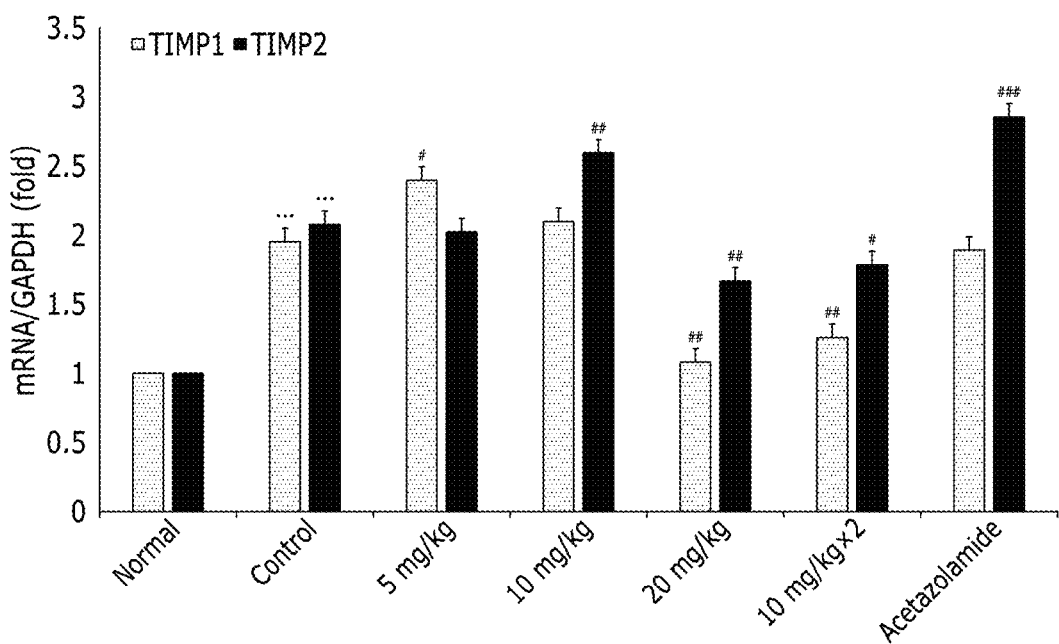

In Experimental Example 10, the expression amounts of these proteins and mRNAs in MMP and TIMP enzymes were measured for the eye tissues of the respective laboratory animals which the measurement of the intraocular pressure was completed, and the results are shown in FIG. 14 to FIG. 17. FIG. 14 and FIG. 15 show protein expression amounts of MMP (MMP2, MMP9) and TIMP (TIMP 1, TIMP2) enzymes, respectively. FIG. 16 and FIG. 17 show mRNA expression levels. In FIG. 14 to FIG. 17, Normal represents the expression level of the animal to which the dexamethasone was not treated in Experimental Example 10, Control represents the expression level of the animal to which only the excipient was administered in Experimental Example 10, and Acetazolamide represents the expression level of the animal to which acetazolamide was administered in Experimental Example 10.

As shown in FIG. 14 to FIG. 17, the protein and mRNA expression levels of the MMP enzyme were significantly decreased in the trabecular meshwork tissue of the animal to which only the excipient was administered or the animal to which acetazolamide, the intraocular pressure reducing agent was administered compared with the normal group and protein and mRNA expression levels of TIMP enzymes were significantly increased. On the other hand, the amount of protein and mRNA expression of MMP enzyme were significantly increased in the trabecular meshwork tissue of the animal administered with 20 mg/kg once a day and 10 mg/kg twice a day of the compound of Example 2 compared to the normal group and the amount of protein and mRNA expression of TIMP enzyme was significantly decreased.

Through the above-mentioned series of experimental results, the adenosine derivatives of the present invention is confirmed to have the effect of reducing the intraocular pressure by inhibiting the production of aqueous humor, which is known to be common to adenosine $A_3$ receptor antagonists, act to reduce intraocular pressure through the dual mechanism by promoting the release of aqueous humor through the inhibition of fibrosis of the trabecular meshwork tissue.

The commercially available glaucoma therapeutic agents lower the intraocular pressure through one of the two pharmacological mechanisms mentioned above, however, since the adenosine derivative of the present invention has the both mechanisms of action, it can be used as a composition highly suitable for the prevention and treatment of glaucoma.

<Experimental Example 13> Physicochemical Characteristic Test of Adenosine Derivative of Present Invention In order to test the physicochemical properties of the adenosine derivatives of the present invention, the compounds of Example 2 were tested in vitro and the results are shown in Table 6. Plasma stability and protein binding were measured using rat and human plasma.

TABLE 6

| Properties (ADME Characteristics) | Value |
|---|---|
| Kinetic solubility@ | 361.0 µM (148.8 µg/ml) |
| Equilibrium solubility | 6.7 µM (2.76 µg/ml) |
| Log P | 3.18 |
| pKa | 11.33 |
| PAMPA | −4.49 |
| Plasma stability | >99.9 (Rat), 98.9 (Human) |
| Plasma protein binding | 90.2(Rat), 98.7 (Human) |

As shown in Table 6, it can be confirmed that the adenosine derivatives of the present invention have absorption, distribution, metabolism and excretion (ADME) characteristics suitable for oral administration by oral preparations.

<Experimental Examples 14 to 18> Pharmacokinetic Test for Oral Administration of Adenosine Derivative of Present Invention In order to test the absorption, distribution, metabolism and excretion (ADME) characteristics of the adenosine derivatives of the present invention after oral administration, the PK (Pharmacokinetic) characteristics of the compound of Example 2 were measured in vivo.

As shown in Table 7, the compound of Example 2 was administered to laboratory animals through different administration methods. Intravenous administration was performed through a tube inserted into the femoral vein, and oral administration was performed using an oral gavage.

TABLE 7

| Experimental Example | Laboratory animal | Administration method |
|---|---|---|
| 14-1 | 8-week-old SD male rat | 5 mg/kg of compound of Example 2 was intravenously administered |
| 14-2 | 8-week-old SD male rat | 5 mg/kg of compound of Example 2 was orally administered |
| 15-1 | 8-week-old SD male rat | 2 mg/kg of compound of Example 2 was intravenously administered |
| 15-2 | 8-week-old SD male rat | 10 mg/kg of compound of Example 2 was orally administered |
| 16 | 8-week-old ICR male mice | 10 mg/kg of compound of Example 2 was orally administered |

TABLE 7-continued

| Experimental Example | Laboratory animal | Administration method |
|---|---|---|
| 17-1 | Dog | 2 mg/kg of compound of Example 2 was intravenously administered |
| 17-2 | Dog | 10 mg/kg of compound of Example 2 was dissolved in a solvent and orally administered |
| 17-3 | Dog | 10 mg/kg of compound of Example 2 was orally administered in powder form in capsules |
| 18-1 | 8-week-old SD male rat | 10 mg/kg of compound of Example 2 was dissolved in 2 mL/kg of 0.5 wt % methylcellulose and orally administered |
| 18-2 | 8-week-old SD male rat | 10 mg/kg of compound of Example 2 was dissolved in a solvent mixed with 5 wt % DMSO, 40 wt % PEG 400, 55 wt % of D.W. and orally administered |

Blood was collected at predetermined time intervals for 24 hours after the administration and centrifuged, plasma was separated, and plasma samples were pretreated with a suitable organic solvent to analyze the concentration by LC-MS/MS. The blood concentration-time data of the compound of Example 2 was analyzed using WinNonlin (Pharsight, USA), and the graphs thereof are shown in FIG. 20 to FIG. 24, and the results of the noncompartmental pharmacokinetic parameters obtained therefrom are shown in Tables 8 to 12. In FIG. 8 to FIG. 12, I.V. represents the intravenous administration group, P.O. represents the oral administration group, and definitions of the respective parameters of Tables 8 to 12 are shown in Table 13.

TABLE 8

| Parameters | I.V., 5 mg/kg | P.O., 5 mg/kg |
|---|---|---|
| $T_{max}$ (h) | NA | 1.33 + 0.577 |
| $C_{max}$ (μg/mL) | NA | 1.45 ± 0.255 |
| $T_{1/2}$ (h) | 3.6 ± 0.589 | 3.26 ± 0.945 |
| $AUC_t$ (μg · h/mL) | 14.04 ± 2.55 | 6.98 ± 0.584 |
| $AUC_\infty$ (μg · h/mL) | 14.11 ± 2.59 | 7.04 ± 0.551 |
| CL (L/h/kg) | 0.363 ± 0.07 | NA |
| $V_{ss}$ (L/kg) | 0.881 ± 0.203 | NA |
| $F_t$ (%) | NA | 49.74 |

NA, not applicable;
ND, not detected;
NC, not calculated

TABLE 9

| Parameters | IV, 2 mg/kg | PO, 10 mg/kg |
|---|---|---|
| $T_{max}$ (hr) | — | 2.42 ± 3.13 |
| $C_{max}$ (μg/mL) | — | 2.71 ± 0.183 |
| $T_{1/2}$ (hr) | 6 ± 2.98 | 3.34 ± 0.075 |
| $AUC_t$ (μg · hr/mL) | 5.2 ± 0.548 | 26.5 ± 5.88 |
| $AUC_\infty$ (μg · hr/mL) | 5.49 ± 0.3 | 26.7 ± 0.0750 |
| CL (L/kg/hr) | 0.365 ± 0.019 | — |
| $V_{ss}$ (L/kg) | 2.27 ± 0.863 | — |
| $F_t$ (%) | — | >99.9 |

TABLE 10

| Parameters | P.O., 10 mg/kg |
|---|---|
| $T_{max}$ (h) | 6.13 ± 3.75 |
| $C_{max}$ (μg/mL) | 8.57 ± 1.52 |
| $T_{1/2}$ (h) | 3.61 ± 0.3 |

TABLE 10-continued

| Parameters | P.O., 10 mg/kg |
|---|---|
| $AUC_t$ (μg · h/mL) | 100 ± 13.2 |
| $AUC_\infty$ (μg · h/mL) | 102 ± 13.5 |
| CL (L/h/kg) | NA |
| $V_{ss}$ (L/kg) | NA |
| $F_t$ (%) | NA |

NA, not applicable;
ND, not detected;
NC, not calculated

TABLE 11

| Parameters | G1, IV, 2 mg/kg | G2, PO, 10 mg/kg | G3, PO, 10 mg/kg |
|---|---|---|---|
| $T_{max}$ (h) | NA | 1.67 ± 0.58 | 2 ± 0 |
| $C_{max}$ (μg/mL) | NA | 0.467 ± 0.073 | 1.14 ± 0.23 |
| $T_{1/2}$ (h) | 2.17 ± 0.867 | 4.21 ± 1.41 | 5.53 ± 3.06 |
| $AUC_t$ (μg · h/mL) | 0.948 ± 0.464 | 3.88 ± 1.03 | 5.64 ± 0.84 |
| $AUC_\infty$ (μg · h/mL) | 1.07 ± 0.62 | 3.99 ± 1.09 | 6.35 ± 0.83 |
| CL (L/h/kg) | 2.27 ± 1.04 | NA | NA |
| $V_{ss}$ (L/kg) | 6.02 ± 0.79 | NA | NA |
| $F_t$ (%) | NA | 82.0 | >99.9 |

NA, not applicable;
ND, not detected;
NC, not calculated

TABLE 12

| Parameters | 0.5% MC, 10 mg/kg | 기존Vehicle, 10 mg/kg |
|---|---|---|
| $T_{max}$ (hr) | 1.33 ± 0.58 | 2.42 ± 3.13 |
| $C_{max}$ (μg/mL) | 5.72 ± 6.11 | 2.71 ± 0.183 |
| $T_{1/2}$ (hr) | 4.56 ± 2.8 | 3.34 ± 0.075 |
| $AUC_t$ (μg · hr/mL) | 40.1 ± 26.8 | 26.5 ± 5.88 |
| $AUC_\infty$ (μg · hr/mL) | 41.4 ± 26.03 | 26.7 ± 0.0750 |
| CL (L/kg/hr) | — | — |
| $V_{ss}$ (L/kg) | — | — |
| $F_t$ (%) | — | — |

TABLE 13

| Parameters | Description |
|---|---|
| $T_{max}$ (hr) | time for Cmax |
| $C_{max}$ (μg/mL) | maximum plasma concentration |
| $T^{1/2}$ (hr) | terminal half-life |
| $AUC_t$ (μg · hr/mL) | areas under the plasma concentration-time curve |
| $AUC_\infty$ (μg · hr/mL) | areas under the plasma concentration-time curve from time |
| CL (L/kg/hr) | total clearance from plasma |
| $V_{ss}$ (L/kg) | steady-state volume of distribution |
| $F_t$ (%) | bioavailability ($AUC_{P.O.}/AUC_{I.V.}$) × 100 |

Figure 18:
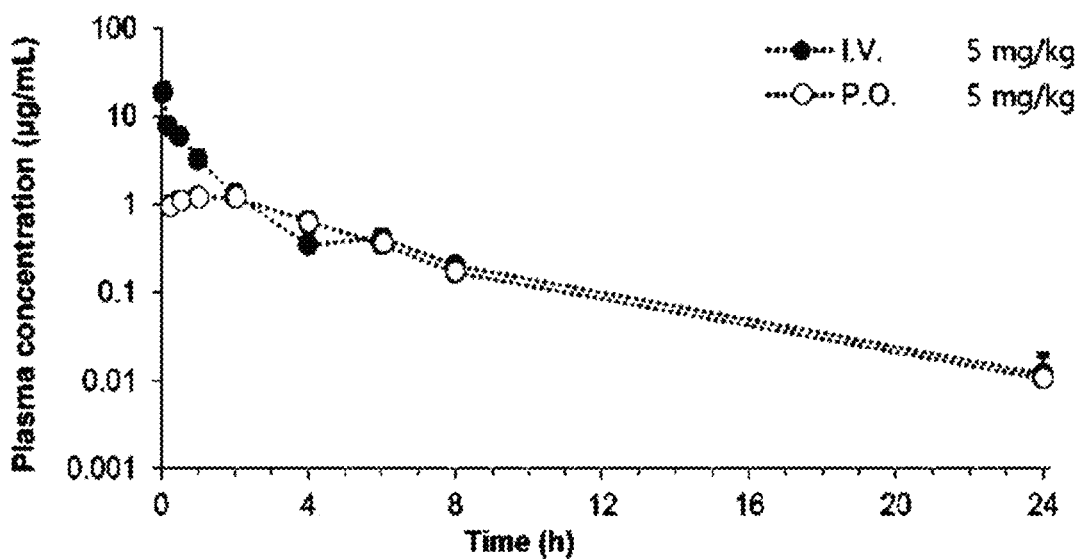
FIG. 18 is a graph obtained from blood concentration-time data of Experimental Example 14 (14-1 and 14-2).
Figure 19:
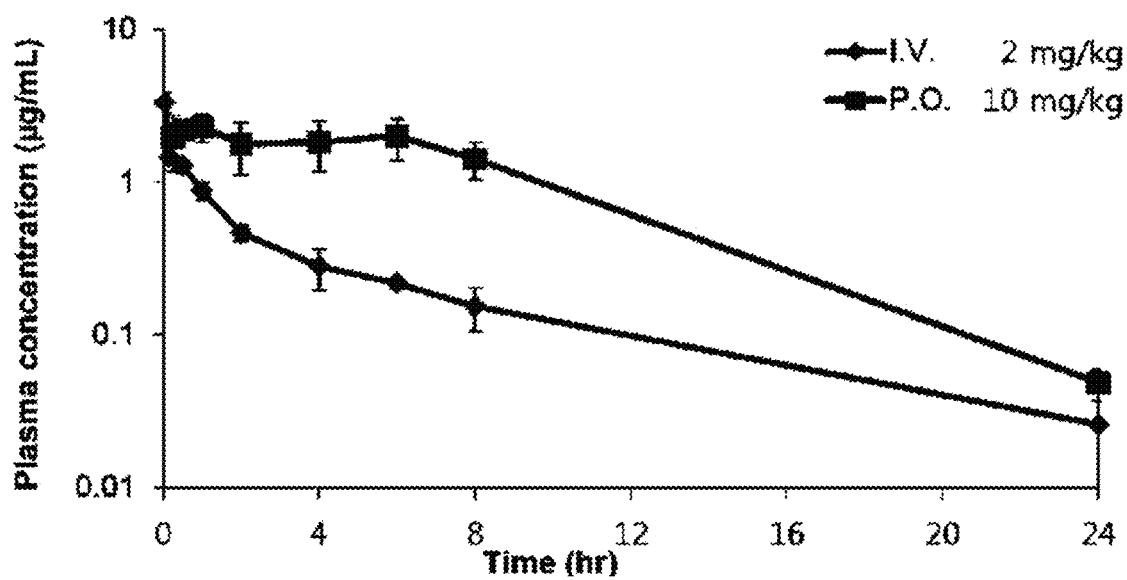
FIG. 19 is a graph obtained from the blood concentration-time data of Experimental Example 15 (15-1 and 15-2).

FIG. 18 and Table 8 are graph and parameter values obtained from the blood concentration-time data of Experimental Example 14 (14-1 and 14-2), respectively, FIG. 19 and Table 9 are graph and parameter values obtained from the blood concentration-time data of Experimental Example 15 (15-1 and 15-2), respectively. As shown in FIG. 18 and FIG. 19 and Tables 8 and 9, it is confirmed that the adenosine derivative of the present invention has a half-life ($T_{1/2}$) of a maximum of 3.34 hours or more for a long time and the bioavailability (Ft) is maximum 99.9% or more as compared with the intravenous administration, and thus it is suitable for oral administration.

Figure 20:
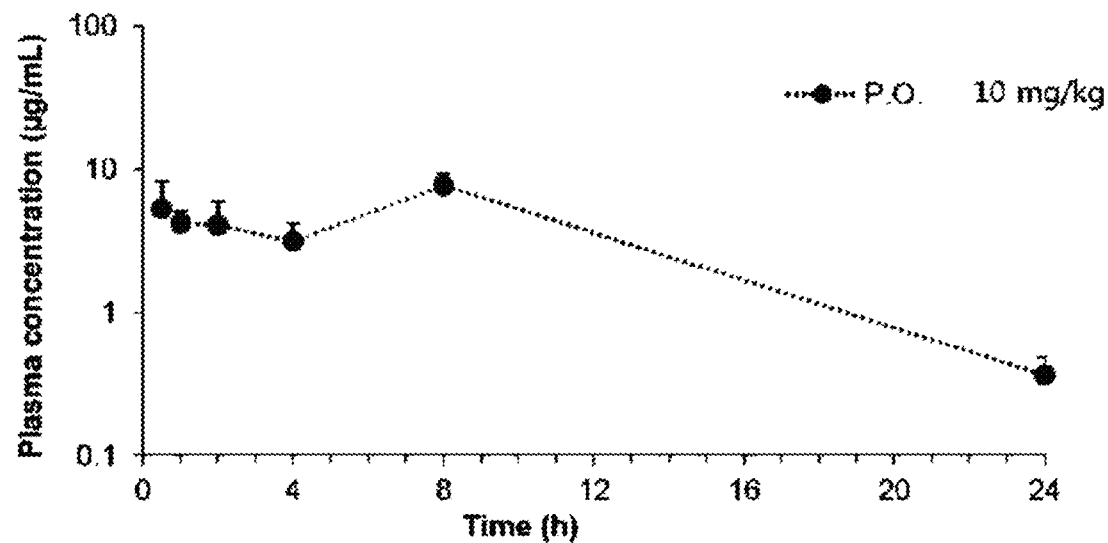
FIG. 20 is a graph obtained from the blood concentration-time data of Experimental Example 16.

FIG. 20 and Table 10 are graph and parameter values obtained from the blood concentration-time data of Experimental Example 16. As shown in FIG. 20 and Table 10, it is confirmed that the adenosine derivative of the present invention has long half-life ($T_{1/2}$) of about 3.61 hours in mice and is suitable for oral administration.

Figure 21:
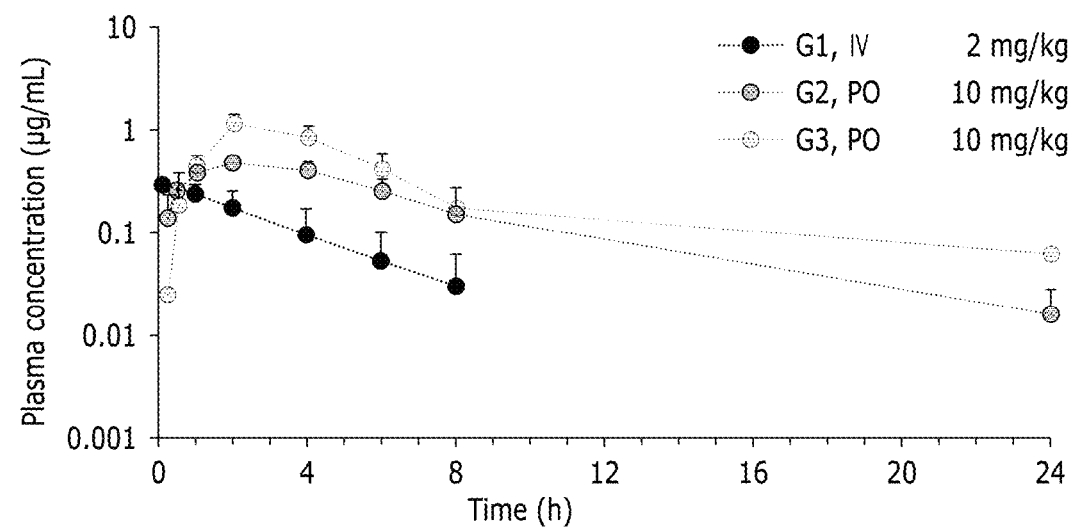
FIG. 21 is a graph obtained from blood concentration-time data of Experimental Example 17 (17-1, 17-2 and 17-3).

FIG. 21 and Table 11 are graph and parameter values obtained from the blood concentration-time data of Experimental Example 17 (17-1, 17-2 and 17-3). In FIG. 21, G2 and G3 represent oral administration after dissolving in a solvent and oral administration in powder form in a capsule, respectively. As shown in FIG. 21 and Table 11, the adenosine derivatives of the present invention have a half-life ($T_{1/2}$) of maximum 5.53 hours or more i.e. is exposed for longer time than rats and mice and are suitable for oral administration and thus are more suitable for oral administration. Particularly, it is confirmed that when it is filled in powder form within a capsule, the half-life ($T_{1/2}$) and bioavailability (Ft) characteristics, etc. are improved.

Figure 22:
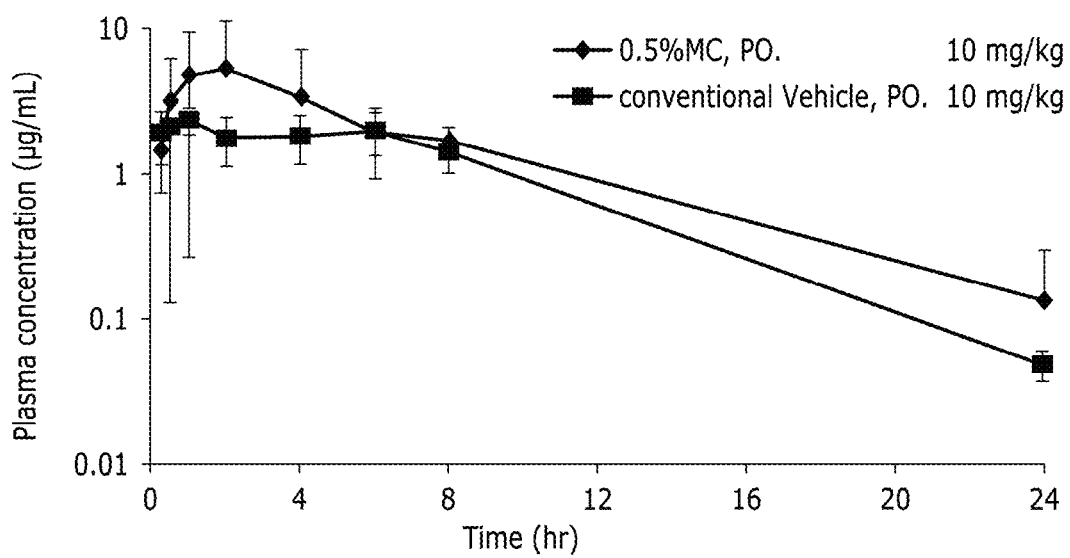
FIG. 22 is a graph obtained from the blood concentration-time data of Experimental Example 18 (18-1 and 18-2).

FIG. 22 and Table 12 are graph and parameter values obtained from the blood concentration-time data of Experimental Example 18 (18-1 and 18-2). As shown in FIG. 22 and Table 12, when the adenosine derivatives of the present invention is orally administered in combination with methyl cellulose (MC), It has better properties than those administered with conventional excipients dimethylsulfoxide (DMSO), polyethylene glycol (PEG), distilled water (D.W.) and the like.

<Experimental Example 19> Toxicity Test of Adenosine Derivative of Present Invention In order to test the toxicity of the adenosine derivatives of the present invention, the compounds of Example 2 were evaluated for cytotoxicity, cardiotoxicity (hERG ligand binding assay), genotoxicity and single dose toxicity.

First, the Cyto XTM cell viability assay kit was used to test the cytotoxicity of the compound of Example 2. As a result of the test, it was evaluated that the $IC_{50}$ by the compound of Example 2 was 10 μM or more in each cell line and was safe for general cytotoxicity.

To test the cardiotoxicity of the compound of Example 2, a non-electrophysiological test was used to evaluate the heart stability through fluorescence polarization evaluation according to the hERG channel protein binding degree of the red fluorescent hERG channel ligand tracer. As a result of the test, the inhibition rate against 10 μM of the compound of Example 2 was 50% or less, which is a standard value, and it was evaluated to be safe against cardiotoxicity.

In order to test the genotoxicity of the compound of Example 2, the gene mutagenicity of the compound of Example 2 was evaluated for each case in the presence and absence of metabolic activation in the presence and absence of metabolic activation using histidine-requiring Salmonella (TA98, TA100, TA1535 and TA1537 strains) and tryptophan-requiring E. coli (WP2uvrA (pKM101) strain) The gene mutagenicity of the compound of Example 2 was evaluated for each case.

As a result of evaluation, as for the compound of Example 2, the number of back-mutation reversion colonies at all doses of each strain did not exceed twice the negative control, regardless of metabolic activation and no dose-dependent increases were observed and in the positive control group, the number of back-mutation reversion colonies for each strain was at least doubled as compared with the negative control. From the above results, the compound of Example 2 was evaluated as safe against genotoxicity.

To test the single dose toxicity of the compound of Example 2, a single dose of 2,000 mg/kg of the compound of Example 2 was administered to each 5 male rats and 5 female rats. As a result of the test, there was no dead animal, and according to the results, the compound of Example 2 was evaluated as safe for single dose toxicity.

Table 14 summarizes the toxicity test results of the adenosine derivatives of the present invention described above. As shown in Table 14, it can be seen that the adenosine derivatives of the present invention are safe against cytotoxicity, cardiotoxicity, genotoxicity and single dose toxicity.

TABLE 14

| Test | toxicity |
|---|---|
| Cytotoxicity Test | Not found |
| Cardiotoxicity test | Not found |
| Genotoxicity test | Not found |
| Single toxicity assessment | |
| Single dose toxicity test | Not found |

<Experimental Example 20> Evaluation of Stability of an Oral Administration Agent Comprising Adenosine Derivatives of Present Invention In order to evaluate the stability of the oral administration agent comprising the adenosine derivative of the present invention, the following experiment was performed.

0.5 wt % methylcellulose, which can be used as an excipient for oral administration, was added to the compound of Example 2, sonicated and homogenized, and then divided into a group to be stored at room temperature or at 4° C., and after 1, 3, 7, and 10 days, the stability was measured by comparing the concentration with 0.5% methyl cellulose as the control group using Waters UPLC and he results are shown in

TABLE 15

| Storage condition | | Stability (%) | | |
|---|---|---|---|---|
| | | 200 µg/ml | 1000 µg/ml | 3000 µg/ml |
| Control | | 100 ± 28.7 | 100 ± 9.55 | 100 ± 5.40 |
| Stored at RT | After 1 day | 84.3 ± 4.10 | 82.7 ± 16.3 | 90.5 ± 6.44 |
| | After 3 days | 76.3 ± 8.12 | 82.7 ± 37.0 | 80.5 ± 5.01 |
| | After 7 days | 80.9 ± 14.6 | 75.4 ± 6.66 | 101 ± 13.2 |
| | After 10 days | 90.3 ± 23.2 | 94.2 ± 9.17 | 92.2 ± 2.17 |
| Stored at 4° C. | After 1 day | 118 ± 21.4 | 76.5 ± 11.7 | 84.8 ± 17.9 |
| | After 3 days | 125 ± 40.2 | 87.6 ± 9.26 | 94.8 ± 2.55 |
| | After 7 days | 88.3 ± 17.3 | 80.1 ± 27.7 | 89.7 ± 8.30 |
| | After 10 days | 93.8 ± 44.8 | 79.5 ± 22.0 | 99.0 ± 3.87 |

As shown in Table 15, when the adenosine derivative of the present invention was prepared as an oral administration agent, the stability of the adenosine derivative was not significantly different according to storage conditions and storage time, and thus, it is confirmed that the adenosine derivative of the present invention was suitable for oral administration by an oral preparation.

While the present invention has been described in connection with what is presently considered to be practical exemplary embodiments, it is to be understood by those skilled in the art that various changes in form and details may be made therein without departing from the spirit and scope of the invention as defined by the appended claims. It is therefore to be understood that the above-described embodiments are illustrative in all aspects and not restrictive.

What is claimed is:

1. A method of treating glaucoma in a subject in need thereof, comprising:
   orally administering a pharmaceutical composition comprising a compound of the Chemical Formula A or a pharmaceutically acceptable salt thereof as an active ingredient to the subject,

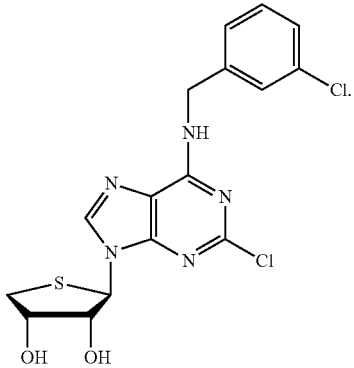

[Chemical Formula A]

wherein the compound is administered to obtain an effective blood concentration for treating glaucoma.

2. The method of claim 1, wherein the pharmaceutical composition further comprises an excipient comprising at least one of methyl cellulose (MC), dimethyl sulfoxide (DMSO), polyethylene glycol (PEG) and distilled water.

3. The method of claim 2, wherein the excipient comprises 0.5 wt % of methyl cellulose.

4. The method of claim 1, wherein the compound of the Chemical Formula A or a pharmaceutically acceptable salt thereof is filled in capsules in powder form.

5. The method of claim 1, wherein the pharmaceutical composition has a dual pharmacological mechanism of inhibiting a production of an aqueous humor in a ciliary body and promoting a release of the aqueous humor through remodeling of trabecular meshwork tissue by a promotion of anti-fibrosis.

* * * * *